(12) United States Patent
Patel et al.

(10) Patent No.: US 7,393,667 B2
(45) Date of Patent: Jul. 1, 2008

(54) STEREOSELECTIVE REDUCTION PROCESS FOR THE PREPARATION OF PYRROLOTRIAZINE COMPOUNDS

(75) Inventors: Ramesh N. Patel, Bridgewater, NJ (US); Linda Nga Hoong Chu, East Brunswick, NJ (US); Robert M. Johnson, Whitehouse Station, NJ (US); Zhiwei Guo, Franklin Park, NJ (US); Yijun Chen, Belle Mead, NJ (US); Steven L. Goldberg, Basking Ridge, NJ (US); Ronald L. Hanson, Morris Plains, NJ (US); Animesh Goswami, Plainsboro, NJ (US); Kishta Katipally, Monmouth Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/421,112

(22) Filed: May 31, 2006

(65) Prior Publication Data

US 2006/0286646 A1 Dec. 21, 2006

Related U.S. Application Data

(60) Provisional application No. 60/686,093, filed on May 31, 2005.

(51) Int. Cl.
*C12P 17/16* (2006.01)
*C07D 253/08* (2006.01)
*C12N 1/00* (2006.01)

(52) U.S. Cl. .................. 435/118; 435/69.1; 435/189; 435/223; 435/254.23; 536/23.2; 544/183

(58) Field of Classification Search .................. None
See application file for complete search history.

(56) References Cited

U.S. PATENT DOCUMENTS

| | | |
|---|---|---|
| 4,373,071 A | 2/1983 | Itakura |
| 4,401,796 A | 8/1983 | Itakura |
| 4,458,066 A | 7/1984 | Caruthers et al. |
| 4,598,049 A | 7/1986 | Zelinka et al. |
| 4,599,311 A | 7/1986 | Kawasaki |
| 4,845,075 A | 7/1989 | Murray et al. |
| 4,870,008 A | 9/1989 | Brake |
| 4,882,279 A | 11/1989 | Cregg |
| 4,931,373 A | 6/1990 | Kawaskaki et al. |
| 4,935,349 A | 6/1990 | McKnight et al. |
| 5,037,743 A | 8/1991 | Welch et al. |
| 5,143,830 A | 9/1992 | Holland et al. |
| 5,162,228 A | 11/1992 | Sumino et al. |
| 5,391,495 A | 2/1995 | Patel et al. |

FOREIGN PATENT DOCUMENTS

| | | |
|---|---|---|
| WO | WO 02/079192 | 10/2002 |
| WO | WO 2004/009601 | 1/2004 |
| WO | WO 2004/009784 | 1/2004 |
| WO | WO 2004/013145 | 2/2004 |

OTHER PUBLICATIONS

Alwine, J. C., et al., "Method for detectionof specific RNAs in agarose gels by transfer to diazobenzyloxymethyl-paper and hybridization with DNA probes", Proc. Natl. Acad. Sci., vol. 74(12), pp. 5350-5354, (1977).
Ausubel. F. M., et al., (Ed), "Current Protocols in Molecular Biology", John Wiley & Sons, Inc., New York, NY, Title page, Table of Content, (1995).
Bird, I. M., "Size Separation and Quantification of mRNA by Northern Analysis", Methods in Molecular Biology, vol. 105, pp. 325-326, (1998).
Bodnar, T. W., et al.,"Formation of a Stable ($n^2$-C,C) Ketene Compound $(C_5H_5)Fe(CO)_2(CH_2CO)^+PF_6^-$ by Carbonylation of an Iron-Methylidene Complex. A Novel Entry into CO-Derived $C_2$ Chemistry", J. Am. Chem. Soc., vol. 105, pp. 5926-5928, (1983).
Botstein, D., et al., "Construction of a Genetic Linkage Map in Man Using Restriction Fragment Length Polymorphisms", Am. J. Hum. Genet. vol. 32, pp. 314-331, (1980).
Brown, C. M., et al., "Introduction to Biotechnology", vol. 10, Blackwell Scientific Publications, Oxford, UK, Title page, Table of Content, (1987).
Carrillo, H. and Lipman, D., "The Multiple Sequence Alignment Problem in Biology", SIAM J. Appl. Math, vol. 48(5), pp. 1073-1082, (1988).
Chen, K., et al., "Regulated Secretion of Prolactin by the Mouse Insulinoma Cell Line βTC-3", Bio/Technology, vol. 13(11), pp. 1191-1197, (1995).
Christen, M. and Crout, D. H. G., "Biotransformation in Organic Synthesis: Applications of Yeast Reduction in the Synthesis of 3,5-Dihydroxy Esters of High Optical Purity", J. Chem. Soc., Chem. Commun., pp. 264-266, (1988).
Crueger, W., et al., "Biotechnology: A Textbook of Industrial Microbiology", 2nd Edition, Sinauer Associates, Inc., Sunderland, MA, Title page, Table of Content, (1990).
Freeman, W.M., "Quantitative RT-PCR: Pitfalls and Potential", Bio/Techniques, vol. 26(1), pp. 112-125, (1999).

(Continued)

*Primary Examiner*—Tekchand Saidha
*Assistant Examiner*—Younus Meah
(74) *Attorney, Agent, or Firm*—Elliott Korsen

(57) ABSTRACT

The invention relates to a process for the enzymatic, stereoselective reduction of ketone compounds to provide chiral alcohols, for example the compound of formula Ib:

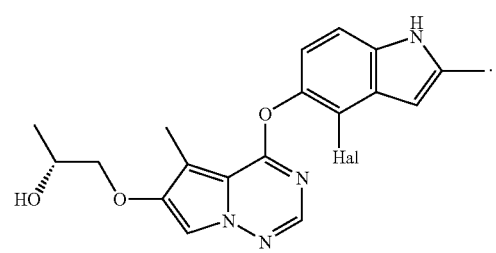

formula Ib

13 Claims, No Drawings

OTHER PUBLICATIONS

Garnier, L., et al., "The Intracellular Domain of the Rabbit Prolactin Receptor is Able to Promote the Secretion of a Passenger Protein via an Unusual Secretory Pathway in Lepidopteran Cells", Bio/Technology, vol. 13(10), pp. 1101-1104, (1995).

Glazer, A. N., et al., "Microbial Biotechnology: Fundamentals of Applied Microbiology", W.H. Freeman and Company, New York, Title page, Table of Content, (1995).

Gleeson, M.A., et al., "Transformation of the Methylotrophic Yeast Hansenula Polymorpha", Journal of General Microbiology, vol. 132, pp. 3459-3465, (1986).

Goeddel, D. V., "Systems for Heterologous Gene Expression", Methods in Enzymology, vol. 185, pp. 3-7, (1990).

Gribskov, M. and Devereux J.,(Ed), "Sequence Analysis Primer", Oxford University Press, New York, Title Page, Table of Contents, (1992).

Griffin, A.M., et al (Eds.), "Computer Analysis of Sequence Data, Part 1", Methods in Molecular Biology, 24 Humana Press, New Jersey, Title page, Table of Content, (1994).

Gusella, J. F., "DNA Polymorphism and Human Disease", Annual Rev. Biochem., vol. 55, pp. 831-854, (1986).

Harlow, E and Lane, D., "Using Antibodies: A Laboratory Manual", Cold Spring Harbor Laboratory Press, Cold Spring Harbor, NY, Title page, Table of Content, (1999).

Harris, E. L. V., et al., (Editor), protein purification methods a practical approach, IRL Press at Oxford University Press, Title page, Table of Content, (1989).

Henikoff, S., et al., "Amino acid substitution matrices from protein blocks", Proc. Natl. Acad. Sci., vol. 89, pp. 10915-10919, (1992).

Hiep, T.T., et al., "Transformation in the Methylotrophic Yeast *Pichia methanolica* utilizing Homologous *ADE1* and Heterologous *Saccharomyces cerevisiae ADE2* and LEU2 Genes as Genetic Markers", Yeast vol. 9, pp. 1189-1197, (1993).

Hunt, J. T., et al., "Discovery of the Pyrrolo[2,1-*f*][1,2,4]triazine Nucleus as a New Kinase Inhibitor Template", J. Med. Chem, vol. 47, pp. 4054-4059, (2004).

Kometani, T., et al., "Relationship between Ethanol Consumption Rate and Prochiral Ketone Reduction Rate in Bakers' Yeast", Journal of Fermentation and Bioengineering, vol. 80(2), pp. 208-210, (1995).

Kubo, T., et al., "Location of a region of the muscarinic acetylcholine receptor involved in selective effector coupling", FEBS Letters, vol. 241(1,2), pp. 119-125, (1998).

Lesk, A. M., (Ed), "Computational Molecular Biology Sources and Methods, for Sequence Analysis", Oxford University Press, New York, Title page, Table of Content, (1988).

Luckow, V. A., et al., "Trends in the Development of Baculovirus Expression Vectors", Bio/Technology, vol. 6, pp. 47-55, (1988).

Male, D., et al., "Advanced Immunology", 2nd Edition, Grower Medical Publishing, New York, Title page, Table of Content, (1991).

Mount, D. W., "Bioinformatics: Sequence and Genome Analysis", Cold Spring Harbor Lab. Press, Cold Spring Harbor, New York, Title page, Table of Content, (2001).

Mullis, K., et al., "Specific Enzymatic Amplification of DNA In Vitro: The Polymerase Chain Reaction", Cold Spring Harbor Symposia on Quantitative Biology, vol. LI, pp. 263-273, (1986).

Needleman, S. B., et al., "A General Method Applicable to the Search for Similarities in the Amino Acid Sequence of Two Proteins", J. Mol. Biol., vol. 48, pp. 443-453, (1970).

Patel, R. N., et al., "Enantioselective microbial reduction of 3,5-dioxo-6-(benzyloxy) hexanoic acid, ethyl ester", Enzyme Microb. Technol., vol. 15, pp. 1014-1021, (1993).

Patel, R. N., et al., "Stereoselective reduction of β-keto esters by *Geotrichum candidum*" Enzyme Microb. Technol., vol. 14, pp. 731-738, (1992).

Patel, R. N., et al. ,"Stereospecific Microbial reduction of 4,5-dihydro-4(4-methoxyphenyl)-6-(trifluoromethyl-1H-1)-benzazepin-2-one", Enzyme Microb. Technol., vol. 13, pp. 906-912, (1991).

Raap, A. K., "Advances in fluorescence in situ hybridization", Mutation Research, vol. 400, pp. 287-298, (1998).

Ren, L., et al., "Lipopolysaccharide-induced expression of IP-10 mRNA in rat brain and in cultured rat astrocytes and microglia", Molecular Brain Research, vol. 59, pp. 256-263, (1998).

Richardson, C. D. (Ed), "Baculovirus Expression Protocols", Methods in Molecular Biology, vol. 39, Humana Press, Totowa, NJ, Title page, Table of Content (1995).

Roitt, I. M., et al, "Immunology", 2nd Edition, C.V. Mosby Company, NY, Title page, Table of Content, (1989).

Rosenberg, I. (ed), "Protein Analysis and Purification Benchtop Techniques", Birkhauser, Boston, MA, Title page, Table of Content, (1996).

Roux, K. H., et al., "Optimization and Troubleshooting in PCR", PCR Methods and Applications, vol. 4, pp. S-185-S194, (1995).

Sambrook, J. et al., "Molecular Cloning A Laboratory Manual, 2nd Edition", Cold Spring Harbor Laboratory Press, Cold Spring Harbor, NY, Title page, Table of Content, (1989).

Smith, D. W. (Ed.), "Biocomputing, Informatics and Genome Projects", Academic Press, New York, Title page, Table of Content, (1993).

Tessier, D. C., "Enhanced secretion from insect cells of a foreign protein fused to the honeybee melittin signal peptide", Gene, vol. 98, pp. 177-183, (1991).

Tom, R. L., et al., "Improved yields of the extracellular domain of the epidermal growth factor receptor produced using the baculovirus expression system by medium replacement following infection", Appl. Microbiol. Biotechnol., vol. 44, pp. 53-58, (1995).

R. L. Tom et al., "Scale-Up of Recombinant Virus and Protein Production in Stirred-Tank Reactors", Methods Molecular Biology, vol. 39, Chapter 12, pp. 203-224, (1995).

Ushio, K., et al., "Stereochemical Control in Microbial Reduction 4. Effect of Cultivation Conditions on the Reduction of β-Keto Esters by Methylotrophic Yeasts", Tetrahedron Letters, vol. 27(23), pp. 2657-2660, (1986).

von Heinje, G., "Sequence Analysis in Molecular Biology Treasure Trove or Trivial Pursuit", Academic Press, Inc., Title page, Table of Content, (1987).

Weiss, S. A., et al., "Insect Cell Culture in Serum-Free Media", Methods in Molecular Biology, vol. 39, Chapter 4, pp. 79-95, (1995).

Zang, M., et al., "Production of Recombinant Proteins in Chinese Hamster Ovary Cells using a Protein-Free Cell Culture Medium", Bio/Technology, vol. 13(4), pp. 389-392, (1995).

STEREOSELECTIVE REDUCTION PROCESS FOR THE PREPARATION OF PYRROLOTRIAZINE COMPOUNDS

This application claims priority benefit under Title 35 § 119(e) of U.S. Provisional Application No. 60/686,093, filed on May 31, 2005, incorporated herein by reference in its entirety.

FIELD OF THE INVENTION

The invention relates to a novel process for the preparation of substituted pyrrolotriazine compounds having a chiral alcohol functionality, by stereoselective reduction of the corresponding oxo compounds. In particular, the process provides for preparation of propan-2-ols such as 1-[4-(4-halo-2-methyl-1H-indol-5-yloxy)-5-methyl-pyrrolo[2,1-f][1,2,4]triazin-6-yloxy]-propan-2-ol, by stereoselective reduction of a corresponding oxo compound. The chiral alcohols produced in accordance with the process of the invention are precursors in molecules therapeutically useful as inhibitors of vascular endothelial growth factor receptor-2, useful as an anticancer agent.

BACKGROUND OF THE INVENTION

Bing-nan Zhou et al. *J. Am Chem. Soc.*, 105, pages 5926-5928, 1983 describe the chemomicrobiological synthesis of L-carnitine, which plays an important role in the human metabolism and transport of long-chain fatty acids. Particularly, this paper teaches the reduction by baker's yeast, i.e. *Saccharomyces cerevisiae*, of ethyl K-chloroacetoacetate to ethyl (S)-4-chloro-3-hydroxybutanoate.

Kazutoshi Ushio et al. *Tetrahedron Letters*, Vol. 27, No. 23, pages 2657-2660, 1986, disclose the reduction of beta-keto esters by methanol grown yeast. This paper teaches that the subject reaction causes dramatic shifts of the enantiomer excess of the resultant product in the direction of the D-isomer. This phenomenon was produced when the reaction was carried out utilizing yeast grown in methanol due to enzymes characteristic of yeast grown in such media.

Markus Christen et al. *J. Chem. Soc. Chem. Commun.* pages 264-266, 1988, discloses the synthesis of four stereoisomers of methyl-6-(p-chlorophenylthio)-3,4-dihydrohexanoate in which the key introduction of chirality was effected by an appropriate yeast reduction. It is stated therein that, although the reduction of beta-keto esters with yeast has been studied extensively, it remains difficult to predict either the absolute configuration of the product(s) or, in particular, the enantiomeric excess likely to be achieved.

Ramesh Patel et al., *Enzyme Microb. Technol.* Vol. 13, pages 906-912, 1991 describe the stereospecific microbial reduction of 4,5-dihydro-4-(4-methoxyphenyl)-6-(trifluoromethyl-1H-1)-benzazepin-2-one. In particular, it is disclosed that a key intermediate (3R-cis)-1,3,4,5-tetrahydro-3-hydroxy-4-(4-methoxyphenyl)-6-(trifluoromethyl)-2H-1-benzazepine-2-one was made by the stereoselective microbial reduction of the parent ketone. It is stated that it was possible by the selection of specific conditions to obtain a single isomer from among four known possibilities.

Ramesh Patel et al., *Enzyme Microb. Technol.*, Vol. 15, pages 1014-1021, 1993, describes the stereoselective reduction of a diketo compound, 3,5-dioxo-6-(benzyloxy) hexanoic acid, methyl ester, to a single enantiomer of the resulting dihydroxy compound.

Ramesh Patel et al., *Enzyme Microb. Technol.* Vol. 14, pages 731-738, 1992, describe a process of heat treating *Geotrichum candidum* to improve the optical purity of the hydroxy product obtained from the reduction of beta-keto esters thereby.

Kometani et al., *Journal of Fermentation and Bioengineering*, Vol. 80, No. 2, pages 208-210, 1995, teaches yeast-mediated bioreduction utilizing ethanol as the energy source. The relationship between the rate of consumption of ethanol and the prochiral ketone reduction rate in Baker's Yeast is examined and it is concluded that ethanol could be applicable to large-scale production of chiral alcohols from prochiral ketones.

Ramesh Patel et al, U.S. Pat. No. 5,391,495, issued Feb. 21, 1995, discloses the stereoselective reduction of certain keto-containing sulfonamide compounds to form the corresponding hydroxyl group-containing compounds utilizing a microorganism or an enzyme capable of catalyzing the reduction. The enzymes named are oxido-reductase or dehydrogenase and the microorganisms are preferably selected from *Hansenula*, *Rhodococcus* and *Norcardia* species.

SUMMARY OF THE INVENTION

The invention is directed to a stereoselective process for the preparation of substituted pyrrolotriazine compounds of formula I and I*, in particular chiral alcohols and analogs thereof,

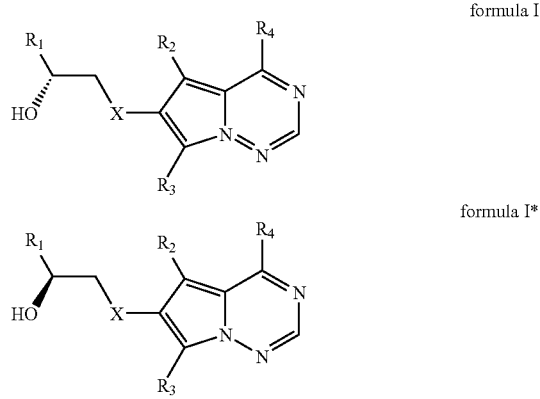

wherein $R_1$, $R_2$, $R_3$, and $R_4$ are each independently selected from $C_1$ to $C_6$ alkyl, aryl or heterocycle, each of which may substituted or unsubstituted, and Hal, wherein halo is selected from F, Cl, Br or J; and $R_4$ may also additionally be selected from Y—$R_5$ wherein Y is selected from O, $NR_1$ or S and $R_5$ is selected from $C_1$ to $C_6$ alkyl, aryl or heterocycle, each of which may substituted or unsubstituted;

X may be absent, or part of the carbon chain, or Z, wherein Z is selected from O, $NR_1$ or S, by enzymatic reduction of the corresponding ketone compounds of formula II

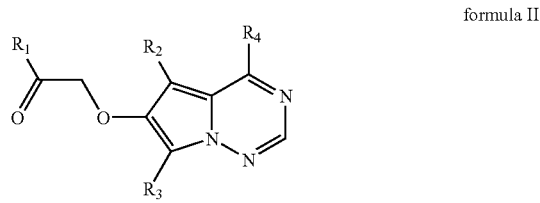

wherein $R_1$, $R_2$, $R_3$, and $R_4$ are as defined above.

In one embodiment, the invention comprises a process for the preparation of compounds according to formula Ia.

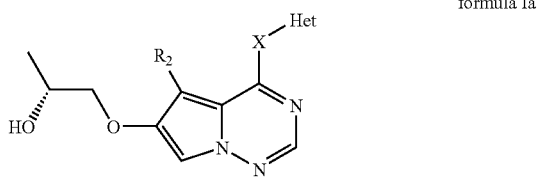

formula Ia wherein
$R_2$ is $C_1$ to $C_6$ alkyl;
X is selected from O, NH or S;
Het is a heterocycle having 1 or 2 rings, which is optionally substituted with alkyl, aryl, or halo;

comprising reducing a ketone compound of formula IIa.

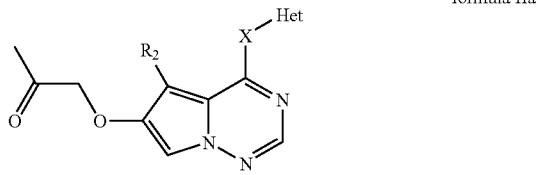

formula IIa

In another embodiment, the substituted pyrrolotriazine compound prepared according to the invention is a compound of formula Ib, which is prepared from a compound of formula IIb.

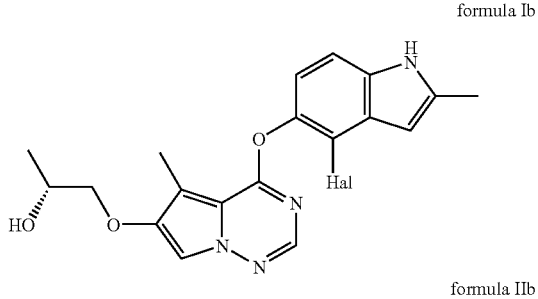

formula Ib

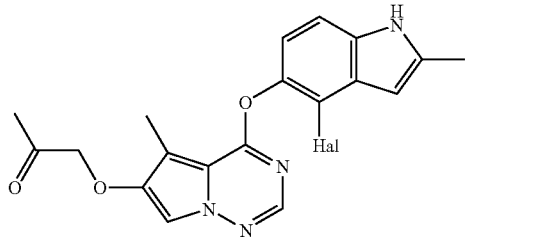

formula IIb

In another embodiment, the compound of formula I is 1-[4-(4-fluoro-2-methyl-1H-indol-5-yloxy)-5-methyl-pyrrolo[2,1-f][1,2,4]triazin-6-yloxy]-propan-2-ol represented by formula Ic,

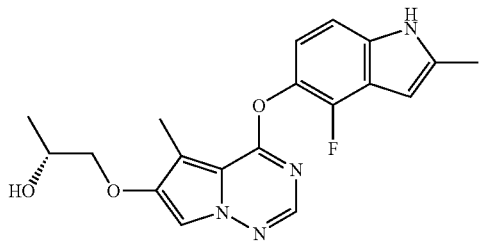

formula Ic which is prepared from 1-[4-(4-fluoro-2-methyl-1H-indol-5-yloxy)-5-methyl-pyrrolo[2,1-f][1,2,4]triazin-6-yloxy]-propan-2-one, formula IIc,

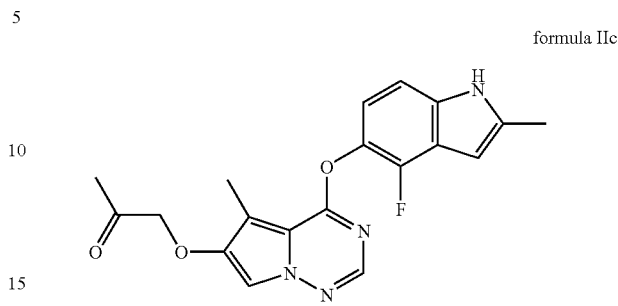

formula IIc by reaction with an oxidoreductase enzyme produced by a microorganism selected from the group consisting of *Rhodococcus*, *Flavobacterium*, *Saccharothrix*, and *Pichia*.

The product is obtained in high yield and in excellent enantiomeric purity. The chiral alcohol produced in accordance with the process of the invention are precursors in molecules therapeutically useful as inhibitors of vascular endothelial growth factor receptor-2 (VEGFR-2), useful as an anticancer agents, as described in Hunt et. al. J. Med. Chem 2004, 47, 4054-4059; and commonly owned and assigned Patent Application Nos. WO 2004/013145 A1, WO 2004/009601 A1, WO 2004/009784 A2, and Patent Application No. WO 02/079192 A1), the entire disclosures of which are herein incorporated by reference.

In another embodiment, the invention comprises a process for the preparation of an oxidoreductase enzyme for the preparation of a compound of formula I from a compound of formula II comprising
(a) either
  i. providing microbial cells selected from the group consisting of *Rhodococcus*, *Flavobacterium*, *Saccharothrix*, and *Pichia* in a growth medium under conditions which allow for expression of an oxidoreductase enzyme, or
  ii. introducing a gene encoding for the oxidoreductase enzyme into a host microorganism for recombinant expression, introducing the host microorganism in a growth medium under conditions which allow for expression of the oxidoreductase enzyme, and allowing it to grow and express the oxidoreductase enzyme;
(b) optionally, extracting the oxidoreductase enzyme from the growth medium containing microbial cells; and
(c) optionally, purifying the oxidoreductase enzyme.

In yet another embodiment the invention comprises an oxidoreductase enzyme having an amino acid sequence according to SEQ ID NO: 1, and variants thereof which may include minor changes of one or more amino acids in the sequence such that the molecule retains oxidoreductase activity.

DETAILED DESCRIPTION OF THE INVENTION

The process of the invention provides an advantageous synthesis for compounds of formula I, formula I*, and analogs thereof. An exemplary compound of formula I with halogen variability is 1-[4-(4-halo-2-methyl-1H-indol-5-yloxy)-5-methyl-pyrrolo[2,1-f][1,2,4]triazin-6-yloxy]-propan-2-ol (formula Ib). A further exemplary compound is 1-[4-

(4-Fluoro-2-methyl-1H-indol-5-yloxy)-5-methyl-pyrrolo[2,1-f][1,2,4]triazin-6-yloxy]-propan-2-ol (formula Ic).

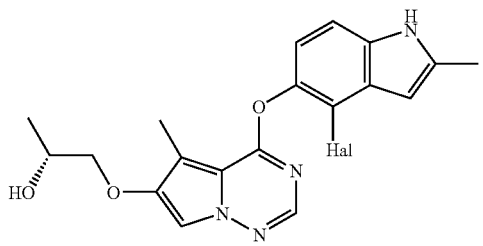

formula Ib

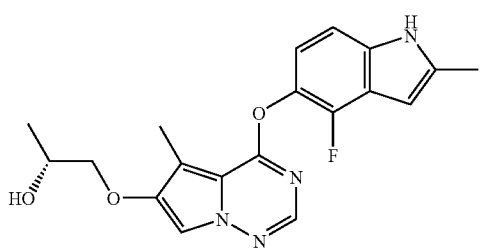

formula Ic

DEFINITIONS

"Halogen" or "Hal" refers to chlorine, bromine, fluorine and iodine, with fluorine being preferred.

The term "alkyl" refers to straight or branched chain hydrocarbon groups or radicals having 1 to 6 carbon atoms, such as methyl, ethyl, n-propyl, i-propyl, n-butyl, i-butyl, t-butyl, pentyl, hexyl, cycloalkyl having 3 to 6 carbon atoms, or any subset of the foregoing, any of which may be optionally substituted.

The term "heterocycle refers to fully saturated or partially or completely unsaturated, including aromatic ("heteroaryl") or nonaromatic substituted or unsubstituted cyclic groups which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

The compounds of formula I may form salts or solvates which are also within the scope of this invention. Reference to a compound of the formula I herein is understood to include reference to salts and solvates thereof unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The terms "fermenting" or "fermentation" are intended to encompass the aerobic or anaerobic growth of a microorganism in a culture medium, as well as the enzymatically controlled transformation of a compound.

"Mixture" means a culture medium to which a substrate and an enzyme or microorganism have been added to facilitate conversion of the substrate by enzymatic, chemical or other means.

"Oxidoreductase enzyme" means an enzyme capable of reducing an oxo group, such as a ketone functional group, contained in the molecular structure of a compound, and would thus encompass those enzymes also known as ketoreductases. Oxidoreductase enzymes according to this definition that may be used in the practice of the invention include any such enzymes derived from or expressed by microorganisms such as those otherwise described herein, as well as any such enzymes expressed via recombinant transformation of a host microorganism that has been encoded with the appropriate genes to provide expression thereof.

"Nucleic acid or "polynucleotide" as used herein refers to purine- and pyrimidine-containing polymers of any length, either polyribonucleotides or polydeoxyribonucleotide or mixed polyribo-polydeoxyribonucleotides. This includes single-and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases. Polynucleotides, e.g., oligonucleotides, include naturally-occurring species or synthetic species formed from naturally-occurring subunits or their close homologs. The term may also refer to moieties that function similarly to polynucleotides, but have non-naturally-occurring portions. Thus, polynucleotides may have altered sugar moieties or inter-sugar linkages. Exemplary among these are phosphorothioate and other sulfur containing species which are known in the art.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" or "complementary sequence" of a nucleic acid sequence as used herein refers to the antisense sequence that participates in Watson-Crick base-pairing with the original sequence.

A "probe" or "primer" refers to a nucleic acid or oligonucleotide that forms a hybrid structure with a sequence in a target region due to complementarily of at least one sequence in the probe or primer with a sequence in the target region.

The term "vector" as used herein refers to a nucleic acid molecule capable of replicating itself and another nucleic acid molecule to which it has been linked. A vector, for example, can be a plasmid, recombinant virus, or transposon.

"Host" includes prokaryotes and eukaryotes. The term includes an organism or cell that is the recipient of a replicable vector.

A "recombinant" polypeptide or peptide refers to an amino acid sequence encoded by a nucleotide sequence described herein.

As used herein, the terms "protein" and "polypeptide" are synonymous. "Peptides" are defined as fragments or portions of polypeptides, preferably fragments or portions having at least one functional activity (e.g., catalytic or antigenic activity) as the complete polypeptide sequence.

The term "antigenic" refers to the ability of a molecule (e.g., a polypeptide or peptide) to bind to its specific antibody, or an antibody fragment, with sufficiently high affinity to form a detectable antigen-antibody complex.

A "sample" as used herein refers to a biological sample, for example, cells, cell culture media, cell components (e.g., cell membranes or cellular organelles), cell extracts (e.g., cytoplasm, cytosol, or nuclear extracts), chemical samples, e.g. of starting materials, additives or reactants, as well as samples obtained from, for example, a laboratory procedure.

The terms "including", "such as", "for example" and the like are intended to refer to exemplary embodiments and not to limit the scope of the invention.

General descriptions of the foregoing terms and others are known in the art. See, e.g., Roitt et al., 1989, *Immunology, 2nd* Edition, C.V. Mosby Company, New York; Male et al., 1991, *Advanced Immunology, 2nd* Edition, Grower Medical Publishing, New York.

One aspect of the invention pertains to isolated oxidoreductase nucleic acids having a nucleotide sequence as shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or variants, modifications, fragments, or complementary sequences thereof. The nucleic acid molecules of the invention can be DNA or RNA (e.g., DNA, RNA, DNA/DNA, and DNA/RNA). In accordance with the invention, preferred nucleic acids are nucleic acids encoding *Pichia angusta, Flavobacterium fuscum, Rhodococcus australis*, oxidoreductases or fragments or functional equivalents thereof. Such nucleic acids can comprise at least 15, 20, 21, 25, 50, 100, 200, 250, 300, 400, 500, or 1500 contiguous nucleotides.

The term "isolated" as used herein refers to a substantially purified molecule (e.g., nucleic acid, polypeptide, peptide, protein fusion, or antibody) that is substantially free of cellular material, culture medium, or other components. Such isolated molecules contain less than 50%, preferably less than 25%, more preferably less than 10%, and most preferably less than 1% of the components with which they were associated.

The term "functional equivalent" is intended to include nucleotide sequences encoding functionally equivalent *P. angusta, Flavobacterium fuscum, Rhodococcus australis, Saccharothrix aerocologenes, Pseudomonas putida, Hansenula polymorpha* oxidoreductases. A functional equivalents of *P. angusta, Flavobacterium fuscum, Rhodococcus australis, Saccharothrix aerocologenes, Pseudomonas putida, Hansenula polymorpha* oxidoreductase includes fragments or variants that perform at least one characteristic function of the enzyme (e.g., catalysis or antigenicity). For example, DNA sequence polymorphisms within the nucleotide sequence of a *P. angusta, Flavobacterium fuscum, Rhodococcus australis, Saccharothrix aerocologenes, Pseudomonas putida, Hansenula polymorpha* oxidoreductase polypeptide, especially those within the third base of a codon, may result in "silent" mutations, which do not affect the encoded amino acid sequence of the polypeptide due to the degeneracy of the genetic code.

Preferred embodiments include an isolated nucleic acid sharing at least 50, 54, 55, 60, 70, 77, 80, 85, 90, 95, 99, or 100% sequence identity with a polynucleotide sequence of *P. angusta, Flavobacteriumfuscum, Pseudomonas putida, Hansenula polymorpha* oxidoreductase (e.g., SEQ ID NOS: 1, SEQ ID NO:2, SEQ ID NO:3 and SEQ ID NO:4). This polynucleotide sequence may be identical to the nucleotide sequence of *P. angusta, Flavobacterium fuscum, Pseudomonas putida, Hansenula polymorpha* oxdioreductase (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8), or may include up to a certain integer number of nucleotide alterations as compared to the reference sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in Lesk, A. M. (Ed.), 1988, *Computational Molecular Biolog*, Oxford University Press, New York; Smith, D. W. (Ed.), 1993, *Biocomputing. Informatics and Genome Projects*, Academic Press, New York; Griffin, A. M., and Griffin, H. G. (Eds.), 1994, *Computer Analysis of Sequence Data, Part I*, Humana Press, New Jersey; von Heinje, G., 1987, *Sequence Analysis in Molecular Biolog*, Academic Press; Gribskov, M. and Devereux, J. (Eds.), 1991, *Sequence Analysis Primer*, M. Stockton Press, New York; and Carillo, H., and Lipman, D., 1988, SIAM *J. Applied Math.* 48:1073.

In accordance with the invention, nucleic acid alterations are selected from the group consisting of at least one nucleotide deletion, substitution, including transition and transversion, insertion, or modification (e.g., via RNA or DNA analogs, dephosphorylation, methylation, or labeling). Alterations may occur at the 5' or 3' terminal positions of the reference nucleotide sequence or anywhere between those terminal positions, interspersed either individually among the nucleotides in the reference sequence or in one or more contiguous groups within the reference sequence.

The invention also encompasses naturally-occurring nucleotide polymorphisms of *P. angusta, Flavobacterium fuscum, Pseudomonas putida, Hansenula polymorpha* oxidoreductase (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8). The genomes of all organisms undergo spontaneous mutation in the course of their continuing evolution generating variant forms of gene sequences (Gusella, 1986, *Ann. Rev. Biochem.* 55:831-854). Restriction fragment length polymorphisms (RFLPs) include variations in DNA sequences that alter the length of a restriction fragment in the sequence (Botstein et al., 1980, *Am. J. Hum. Genet.* 32, 314-331). Short tandem repeats (STRs) include tandem di-, tri- and tetranucleotide repeated motifs, also termed variable number tandem repeat (VNTR) polymorphisms.

Single nucleotide polymorphisms (SNPs) are far more frequent than RFLPS, STRs, and VNTRs. SNPs may occur in protein coding (e.g., exon), or non-coding (e.g., intron, 5'UTR, and 3'UTR) sequences. SNPs in protein coding regions may comprise silent mutations that do not alter the amino acid sequence of a protein. Alternatively, SNPs in protein coding regions may produce conservative or non-conservative amino acid changes, described in detail below. In non-coding sequences, SNPs may also result in defective protein expression (e.g., as a result of defective splicing). Other single nucleotide polymorphisms have no phenotypic effects.

Further encompassed by the invention are nucleic acid molecules that share moderate homology with the *P. angusta, Flavobacterium fuscum, Pseudomonas putida, Hansenula polymorpha* nucleic acid sequence (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8 or a complementary sequence), and hybridize to a *P. angusta, Flavobacterium* fuscum, Pseudomonas putida, Hansenula polymorpha oxidoreductase nucleic acid molecule under moderate stringency hybridization conditions. More preferred are nucleic acid molecules that share substantial homology with a *P. angusta, Flavobacterium fuscum, Pseudomonas putida, Hansenula polymorpha* oxidoreductase nucleic acid sequence (e.g., SEQ ID NO: 1, SEQ ID NO:2, SEQ ID NO:3, SEQ ID NO:4, SEQ ID NO:5, SEQ ID NO:6, SEQ ID NO:7, SEQ ID NO:8 or a complementary sequence) and hybridize to *P. angusta, Flavobacterium fuscum, Pseudomonas putida, Hansenula polymorpha* oxidoreductase nucleic acid molecules under high stringency hybridization conditions.

As used herein, the phrase "moderate homology" refers to sequences which share at least 60% sequence identity with an oxidoreductase sequence (e.g., SEQ ID NO:1), whereas the phrase "substantial homology" refers to sequences that share at least 90% sequence identity with a ketoreductase sequence. It is recognized, however, that polypeptides and the nucleic acids encoding such polypeptides containing less than the above-described level of homology arising as splice variants or that are modified by conservative amino acid substitutions (or substitution of degenerate codons) are contemplated to be within the scope of the invention.

The phrase "hybridization conditions" is used herein to refer to conditions under which a double-stranded nucleic acid hybrid is formed from two single nucleic acid strands, and remains stable. As known to those of skill in the art, the stability of the hybrid sequence is reflected in the melting temperature ($T_m$) of the hybrid (see F. M. Ausubel et al. (Eds.), 1995, Current Protocols in Molecular Biology, John Wiley and Sons, Inc., New York, N.Y.). The $T_m$ decreases approximately 0.5° C. to 1.5° C. with every 1% decrease in sequence homology. In general, the stability of a hybrid sequence is a function of the length and guanine/cytosine content of the hybrid, the sodium ion concentration, and the incubation temperature. Typically, the hybridization reaction is initially performed under conditions of low stringency, followed by washes of varying, but higher, stringency. Reference to hybridization stringency relates to such washing conditions.

In accordance with the invention, "high stringency" conditions can be provided, for example, by hybridization in 50% formamide, 5×Denhardt's solution, 5×SSPE, and 0.2% SDS at 42° C., followed by washing in 0.1×SSPE and 0.1% SDS at 65° C. By comparison, "moderate stringency" can be provided, for example, by hybridization in 50% formamide, 5×Denhardt's solution, 5×SSPE, and 0.2% SDS at 42° C., followed by washing in 0.2×SSPE and 0.2% SDS at 65° C. In addition, "low stringency" conditions can be provided, for example, by hybridization in 10% formamide, 5×Denhardt's solution, 6×SSPE, and 0.2% SDS at 42° C., followed by washing in 1×SSPE and 0.2% SDS at 50° C. It is understood that these conditions may be varied using a variety of buffers and temperatures well known to those skilled in the art.

In a preferred embodiment of the invention, the nucleic acid is a DNA molecule encoding at least a fragment of an oxidoreductase (SEQ ID NO:2). A nucleic acid molecule encoding an oxidoreductase can be obtained from mRNA present in cells. It may also be possible to obtain nucleic acid molecules encoding an oxidoreductase from *Pichia angusta, Flavobacterium fuscum, Pseudomonas putida, Hansenula polymorpha* genomic DNA. In addition, a nucleic acid encoding a oxidoreductase can be cloned from either a cDNA or a genomic library in accordance with the protocols described in detail herein.

Nucleic acids encoding *P. angusta, Flavobacterium fuscum, Rhodococcus australis, Saccharothrix aerocologenes, Pseudomonas putida, Hansenula polymorpha* oxidoreductase enzymes can also be cloned using established polymerase chain reaction (PCR) techniques (see K. Mullis et al., 1986, Cold Spring Harbor Symp. Quant. Biol. 51:260; K. H. Roux, 1995, PCR Methods Appl. 4:S185) in accordance with the nucleic acid sequence information provided herein. For example, PCR techniques can be used to produce the nucleic acids of the invention, using either RNA (e.g., mRNA) or DNA (e.g., genomic DNA) as templates. Primers used for PCR can be synthesized using the sequence information provided herein and can further be designed to introduce appropriate new restriction sites, if desirable, to facilitate incorporation into a given vector for recombinant expression.

The nucleic acid molecules of the invention, or fragments thereof, can also be chemically synthesized using standard techniques. Various methods of chemically synthesizing polydeoxynucleotides are known, including solid-phase synthesis which, like peptide synthesis, has been fully automated in commercially available DNA synthesizers (see, for example, U.S. Pat. No. 4,598,049 to Itakura et al.; U.S. Pat. No. 4,458,066 to Caruthers et al.; U.S. Pat. Nos. 4,401,796 and 4,373,071 to Itakura).

It will be appreciated by one skilled in the art that variations in one or more nucleotides (up to about 3-4% of the nucleotides) of the nucleic acid molecules encoding a *P. angusta, Flavobacterium fuscum, Rhodococcus australis, Saccharothrix aerocologenes, Pseudomonas putida, Hansenula polymorpha* oxidoreductase may exist among organisms within a population due to natural allelic variation. Any and all such nucleotide variations and resulting amino acid polymorphisms are within the scope of the invention. Furthermore, there may be one or more isoforms or related family members of the *P. angusta, Flavobacterium fuscum, Rhodococcus australis, Saccharothrix aerocologenes, Pseudomonas putida, Hansenula polymorpha* oxidoreductases described herein. Such isoforms or family members are defined as polypeptides that are related in function and amino acid sequence to a oxidoreductase (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8), but encoded by genes at different loci. In addition, it is possible to modify the DNA sequence of the oxidoreductase gene using genetic techniques to produce proteins or peptides with altered amino acid sequences.

DNA sequence mutations can be introduced into a nucleic acid encoding an oxidoreductase by any one of a number of methods, including those for producing simple deletions or insertions, systematic deletions, insertions or substitutions of clusters of bases or substitutions of single bases, to generate desired variants. Mutations of the oxidoreductase nucleic acid molecule to generate amino acid substitutions or deletions are preferably obtained by site-directed mutagenesis.

Site directed mutagenesis systems are well known in the art, and can be obtained from commercial sources. Guidance in determining which amino acid residues may be substituted, inserted, or deleted without abolishing biological or immunological activity may be found using computer programs well known in the art, for example, DNASTAR software. Mutant forms of the oxidoreductase nucleic acid molecules are considered within the scope of the invention, where the expressed polypeptide or peptide is capable catalytic or antigenic activity.

A fragment of the nucleic acid molecule encoding an oxidoreductase is defined as a nucleotide sequence having fewer nucleotides than the nucleotide sequence encoding the entire amino acid sequence of the enzyme. In one embodiment of the invention, a nucleic acid molecule corresponding to a fragment of a *P. angusta, Flavobacterium fuscum, Rhodococ-* cus australis, Saccharothrix aerocologenes, Pseudomonas putida, Hansenula polymorpha oxidoreductase nucleic acid sequence can be used as a probe for assaying a biological sample (e.g., from cells or cell extracts), the expression of one or more enzymes, or as a primer for DNA sequencing or PCR amplification. Preferably, such fragments are at least 8, 12, 15, 20, 21, or 25 contiguous nucleotides in length.

In certain embodiments, the nucleic acid molecules of the invention may include linker sequences, modified restriction endonuclease sites, and other sequences useful for molecular cloning, expression, or purification of recombinant protein or fragments thereof. Nucleic acid molecules in accordance with the invention may also be conjugated with radioisotopes, or chemiluminescent, fluorescent, or other labeling compounds (e.g., digoxigenin). In addition, the nucleic acid molecules of the invention may be modified by nucleic acid modifying enzymes, for example, kinases or phosphatases. These and other modifications of nucleic acid molecules are well known in the art. In addition, a nucleic acid molecule that encodes a *P. angusta, Flavobacterium fuscum, Rhodococcus australis, Saccharothrix aerocologenes, Pseudomonas putida, Hansenula polymorpha* oxidoreductase, or a functional fragment thereof, can be ligated to a heterologous sequence to encode a fusion protein (also called a chimeric protein) as described in detail herein.

Vectors and Host Cells

Another aspect of the invention pertains to vectors comprising a nucleic acid encoding an oxidoreductase as described herein operably linked to at least one regulatory sequence. "Operably linked" is intended to mean that the nucleotide acid sequence is linked to a regulatory sequence in a manner that allows expression of the nucleotide sequence (i.e., production of mRNA and/or amino acid sequences). Regulatory sequences are known in the art and are selected to direct expression of the desired protein in an appropriate host cell or cell-free expression system. Accordingly, the term regulatory sequence includes promoters, enhancers and other expression control elements (see D. V. Goeddel, 1990, *Methods Enzymol.* 185:3-7). It should be understood that the design of the expression vector may depend on such factors as the choice of the host cell or expression system to be utilized and/or the type of polypeptide desired to be expressed.

Suitable expression vectors include, but are not limited to, pUC, pBluescript (Stratagene), pET (Novagen, Inc.), as well as pREP, pSE420, and pLEX (Invitrogen). Vectors can contain one or more replication and inheritance systems for cloning or expression, one or more markers for selection in the host, e.g. antibiotic resistance, and one or more expression cassettes. The inserted coding sequences can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods. Preferred replication and inheritance systems include M13, ColE1, SV40, baculovirus, lambda, adenovirus, CEN ARS, 2 µm, ARS, and the like. Several regulatory elements (e.g., promoters) have been isolated and shown to be effective in the transcription and translation of heterologous proteins in the various hosts. Such regulatory regions, methods of isolation, manner of manipulation, etc. are known in the art. Non-limiting examples of bacterial promoters include the β-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac UV5 promoters.

Non-limiting examples of yeast promoters include the 3-phosphoglycerate kinase promoter, glyceraldehyde-3-phosphate dehydrogenase (GAFDH or GAP) promoter, galactokinase (GAL1) promoter, galactoepimerase promoter, and alcohol dehydrogenase (ADH1) promoter. Suitable promoters for mammalian cells include, without limitation, viral promoters, such as those from Simian Virus 40 (SV40), Rous sarcoma virus (RSV), adenovirus (ADV), and bovine papilloma virus (BPV). Alternatively, the endogenous bacterial regulatory elements (e.g., in SEQ ID NO:1, SEQ ID NO:2, SEQ ID NO:3, SEQ ID NO:4, SEQ ID NO:5, SEQ ID NO:6, SEQ ID NO:7, SEQ ID NO:8 etc.) can be used.

Eukaryotic cells may also require terminator sequences, polyadenylation sequences, and enhancer sequences that modulate gene expression. Sequences that cause amplification of the gene may also be desirable. These sequences are well known in the art. Furthermore, sequences that facilitate secretion of the recombinant product from cells, including, but not limited to, bacteria, yeast, and animal cells, such as secretory signal sequences and/or preprotein or proprotein sequences, may also be included in accordance with established methods. Secretory signal sequences are generally positioned 5' to the nucleotide sequence encoding the protein of interest, although certain signal sequences can be positioned 3' to the nucleotide sequence of interest (see, e.g., Welch et al., U.S. Pat. No. 5,037,743; Holland et al., U.S. Pat. No. 5,143,830). Cell-specific secretory signals can be used with certain cell types (e.g., yeast cells).

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that 1) confer resistance to antibiotics or other toxic substances, e.g., ampicillin, neomycin, methotrexate, etc.; 2) complement auxotrophic deficiencies, or 3) supply critical nutrients not available from complex media, e.g., the gene encoding D-alanine racemase for *Bacilli*. Markers may be an inducible or non-inducible gene and will generally allow for positive selection. Non-limiting examples of markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable cell-free expression systems for use with the invention include, without limitation, rabbit reticulocyte lysate, wheat germ extract, canine pancreatic microsomal membranes, *E. coli* S30 extract, and coupled transcription/translation systems (Promega Corp.). Suitable host cells include bacteria, fungi, yeast, plant, insect, and animal, mammalian, and human cells. Specifically included are SF9, C129, 293, NIH 3T3, CHO, COS, HeLa, and *Neurospora* cells. Insect cell systems (i.e., lepidopteran host cells and baculovirus expression vectors) (Luckow and Summers, 1988, *Biotechnology* 6:47-55) are also included.

Preferred host cells include fungal cells, such as *Aspergillus* (*A. niger, A. oryzae*, and *A. fumigatus*), *Fusarium venenatum, Schizosaccharomyces pombe, Saccharomyces cerevisiae, Kluyveromyces lactis, Kluyveromyces fragilis, Ustilago maydis, Candida* (e.g., *C. albicans, C. methylica, C. boidinii, C. tropicalis, C. wickerhamii, C. maltosa*, and *C. glabrata*), *Hansenula* (e.g., *H. anomala, H. polymorpha, H. wingei, H.*

*jadinii* and *H. saturnus*); and *Pichia* (e.g., *P. angusta, P. pastoris, P. anomala, P. stipitis, P. methanolica*, and *P. guilliermondii*) cells. Particularly preferred are bacterial cells, such as *Staphylococcus aureus, Escherichia coli, Bacillus* (e.g., *B. licheniformis, B. amyloliquefaciens*, and *B. subtilis*) and *Streptomyces* (e.g., *Streptomyces lividans* and *Streptomyces coelicolor*) cells.

In general, host cells can be transformed, transfected, or infected as appropriate by any suitable method including electroporation, calcium chloride-, lithium chloride-, lithium acetate/polyethylene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, e.g., by injection (see, Kubo et al., 1988, *FEBS Letts.* 241:119).

Methods for transforming *S. cerevisiae* cells with exogenous DNA and producing recombinant proteins therefrom are found in, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; Murray et al., U.S. Pat. No. 4,845,075, and Kawasaki et al., U.S. Pat. No. 4,931,373). Transformation methods for other yeasts, including *H. polymorpha/P. angusta, S. pombe, K. lactis, K. fragilis, U. maydis, P. pastoris, P. methanolica/C. methylica*, and *C. maltosa* are known in the art (see, for example, Gleeson et al., 1986, *J. Gen. Microbiol.* 132:3459-3465; Cregg, U.S. Pat. No. 4,882,279; and Hiep et al., 1993, *Yeast* 9:1189-1197). *Aspergillus* cells can be transformed according to the methods of McKnight et al., U.S. Pat. No. 4,935,349, while *Acremonium chrysogenum* cells can be transformed in accordance with Sumino et al., U.S. Pat. No. 5,162,228. In general, host cells may integrate the nucleic acid molecules of this invention into chromosomal loci. Alternatively, the host cells may maintain the nucleic acid molecules via episomal vectors.

In one embodiment, an expression vector comprises a nucleic acid encoding at least a fragment of an oxidoreductase. In another embodiment, the expression vector comprises a DNA sequence encoding at least a fragment of a oxidoreductase fused in-frame to a DNA sequence encoding a heterologous polypeptide or peptide. Such expression vectors can be used to transfect host cells to thereby produce oxidoreductase polypeptides or peptides, including fusion proteins or peptides encoded by nucleic acid molecules as described below.

Several well-established techniques can be used to determine the expression levels and patterns of the oxidoreductase. For example, mRNA levels can be determined utilizing Northern blot analysis (J. C. Alwine et al., 1977, *Proc. Natl. Acad. Sci. USA* 74:5350-5354; I. M. Bird, 1998, *Methods Mol. Biol.* 105:325-36), whereby poly(A)$^+$ RNA is isolated from cells, separated by gel electrophoresis, blotted onto a support surface (e.g., nitrocellulose or Immobilon-Ny+(Millipore Corp., Bedford, Mass.)), and incubated with a labeled (e.g., fluorescently labeled or radiolabeled) oligonucleotide probe that is capable of hybridizing with the mRNA of interest.

Alternatively, mRNA levels can be determined by quantitative (for review, see W. M. Freeman et al., 1999, *Biotechniques* 26:112-122) or semi-quantitative RT-PCR analysis (Ren et al., *Mol. Brain Res.* 59:256-63). In accordance with this technique, poly(A)$^+$ RNA is isolated from cells, used for cDNA synthesis, and the resultant cDNA is incubated with PCR primers that are capable of hybridizing with the template and amplifying the template sequence to produce levels of the PCR product that are proportional to the cellular levels of the mRNA of interest. Another technique, in situ hybridization, can also be used to determine mRNA levels (reviewed by A. K. Raap, 1998, *Mutat. Res.* 400:287-298). In situ hybridization techniques allow the visual detection of mRNA in a cell by incubating the cell with a labeled (e.g., fluorescently labeled or digoxigenin labeled) oligonucleotide probe that hybridizes to the mRNA of interest, and then examining the cell by microscopy.

Oxidoreductase fragments, modifications, or variants can be also be assessed directly by well-established techniques. For example, host cell expression of the recombinant polypeptides can be evaluated by western blot analysis using antibodies specifically reactive with these polypeptides (see above). Production of secreted forms of the polypeptides can be evaluated by immunoprecipitation using monoclonal antibodies that are specifically reactive the polypeptides. Other, more preferred, assays take advantage of the functional characteristics of the oxidoreductase.

Polypeptides

A further aspect of the invention pertains to oxidoreductase polypeptides (e.g., recombinant polypeptides). The invention encompasses a oxidoreductase polypeptide (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8) and fragments and functional equivalents thereof. Such polypeptides can comprise at least 5, 12, 20, 21, 25, 30, 32, 35, 50, 100, 170, 200, 210, 300, or 600 contiguous amino acid residues. Preferred are polypeptides that share moderate homology with a oxidoreductase polypeptide (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8). More preferred are polypeptides that share substantial homology with an oxidoreductase polypeptide.

The term "functional equivalent" is intended to include proteins which differ in amino acid sequence from the oxidoreductase polypeptide (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8), but where such differences result in a modified protein which performs at least one characteristic function of polypeptide (e.g., catalytic or antigenic activity). For example, a functional equivalent of oxidoreductase polypeptide may have a modification such as a substitution, addition or deletion of an amino acid residue which is not directly involved in the function of this polypeptide. Various modifications of the oxidoreductase polypeptide to produce functional equivalents of these polypeptides can be made in accordance with established methods.

It is also possible to modify the structure of a oxidoreductase polypeptide for such purposes as increasing solubility, enhancing reactivity, or increasing stability (e.g., shelf life ex vivo and resistance to proteolytic degradation in vivo). Such modified proteins are considered functional equivalents of a oxidoreductase polypeptide as defined herein. Preferably, oxidoreductase polypeptides are modified so that they retain catalytic activity. Those residues shown to be essential for activity can be modified by replacing the essential amino acid with another, preferably similar amino acid residue (a conservative substitution) whose presence is shown to enhance, diminish, but not eliminate, or not effect receptor interaction. In addition, those amino acid residues that are not essential for catalysis can be modified by being replaced by another amino acid whose incorporation may enhance, diminish, or not effect reactivity.

Preferred polypeptide embodiments further include an isolated polypeptide comprising an amino acid sequence sharing at least 50, 54, 55, 60, 70, 80, 85, 86, 90, 95, 97, 98, 99, 99.5 or 100% identity with the amino acid sequence of oxidoreductase (SEQ ID NO:1, SEQ ID NO:2, SEQ ID NO:3, SEQ ID NO:4, SEQ ID NO:5, SEQ ID NO:6, SEQ ID NO:7, SEQ ID NO:8). This polypeptide sequence may be identical to the sequence of oxidoreductase (SEQ ID NO:1, SEQ ID NO:2, SEQ ID NO:3, SEQ ID NO:4, SEQ ID NO:5, SEQ ID NO:6, SEQ ID NO:7, SEQ ID NO:8), or may include up to a certain integer number of amino acid alterations as compared to the reference sequence.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, *Bioinformatics: Sequence and Genome Analysis*, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch, 1970, *J Mol. Biol.* 48:443-453; 2) BLOSSUM62 comparison matrix from Hentikoff and Hentikoff, 1992, *Proc. Natl. Acad. Sci. USA* 89:10915-10919; 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps). Alternatively, polypeptide sequence identity can be calculated using the following equation: % identity=(the number of identical residues)/(alignment length in amino acid residues)*100. For this calculation, alignment length includes internal gaps but does not include terminal gaps.

In accordance with the invention, polypeptide sequences may be identical to the sequence of oxidoreductase (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8), or may include up to a certain integer number of amino acid alterations. Polypeptide alterations are selected from the group consisting of at least one amino acid deletion, substitution, including conservative and non-conservative substitution, or insertion. Alterations may occur at the amino- or carboxy-terminal positions of the reference polypeptide sequence or anywhere between those terminal positions, interspersed either individually among the amino acids in the reference sequence or in one or more contiguous groups within the reference sequence. In specific embodiments, polypeptide variants may be encoded by oxidoreductase nucleic acids comprising single nucleotide polymorphisms and/or alternate splice variants.

Oxidoreductase polypeptides may also be modified by conjugation with a label capable of providing a detectable signal, either directly or indirectly, including, for example, radioisotopes and fluorescent compounds. Non-limiting examples of fluorescent compounds include Cy3, Cy5, GFP (e.g., EGFP, DsRed, dEFP, etc. (CLONTECH), Alexa, BODIPY, fluorescein (e.g., FluorX, DTAF, and FITC), rhodamine (e.g., TRITC), auramine, Texas Red, AMCA blue, and Lucifer Yellow. Suitable isotopes include, but are not limited to, $^{3}H$, $^{14}C$, $^{32}P$, $^{35}S$, $^{36}Cl$, $^{51}Cr$, $^{57}Co$, $^{51}Co$, $^{5}Fe$, $^{90}Y$, $^{125}I$, $^{131}I$, and $^{116}Re$.

The invention also relates to isolated, synthesized and/or recombinant portions or fragments of a oxidoreductase polypeptide (e.g., SEQ ID NO:2), as described herein.

Polypeptide fragments (i.e., peptides) can be made which have full or partial function on their own, or which when mixed together (though fully, partially, or nonfunctional alone), spontaneously assemble with one or more other polypeptides to reconstitute a functional protein having at least one functional characteristic of a oxidoreductase of this invention. In addition, oxidoreductase polypeptide fragments may comprise, for example, one or more domains of the polypeptide (e.g., a short chain dehydrogenase domain) disclosed herein.

The polypeptides of the invention, including function-conservative variants, may be isolated from wild-type or mutant *P. angusta, Flavobacterium fuscum, Rhodococcus australis, Saccharothrix aerocologenes, Pseudomonas putida, Hansenula polymorpha* cells, from heterologous organisms or cells (e.g., bacteria, yeast, insect, plant, or mammalian cells) comprising recombinant oxidoreductase, or from cell-free translation systems (e.g., wheat germ, microsomal membrane, or bacterial extracts) in which a oxidoreductase protein-coding sequence has been introduced and expressed. Furthermore, the polypeptides may be part of recombinant fusion proteins. The polypeptides can also, advantageously, be made by synthetic chemistry. Polypeptides may be chemically synthesized by commercially available automated procedures, including, without limitation, exclusive solid phase synthesis, partial solid phase methods, fragment condensation or classical solution synthesis.

Isolation of Polypeptides

Yet another aspect of the invention pertains to methods of isolating oxidoreductase polypeptides, or variants, modifications, or fragments thereof from biological samples (e.g., cells, cell extracts or lysates, cell membranes, growth media, etc.). Fragments of ketoreductase polypeptides (i.e., peptides) include fragments, preferably, having the same or equivalent function or activity as the full-length polypeptide. Both naturally occurring and recombinant forms of the oxidoreductase polypeptides or peptides may be used in the methods according to the invention. Methods for directly isolating and purifying polypeptides or peptides from cellular or extracellular lysates are well known in the art (see E. L. V. Harris and S. Angal (Eds.), 1989, *Protein Purification Methods: A Practical Approach*, IRL Press, Oxford, England). Such methods include, without limitation, preparative disc-gel electrophoresis, isoelectric focusing, high-performance liquid chromatography (HPLC), reversed-phase HPLC, gel filtration, ion exchange and partition chromatography, and countercurrent distribution, and combinations thereof.

In addition, antibody-based methods can be used to isolate natural or recombinantly produced oxidoreductase polypeptides or peptides. Antibodies that recognize these polypeptides, or peptides derived therefrom, can be produced and isolated using methods known and practiced in the art (see below). oxidoreductase polypeptides or peptides can then be purified from a crude lysate by chromatography on antibody-conjugated solid-phase matrices (see E. Harlow and D. Lane, 1999, *Using Antibodies: A Laboratory Manual*, Cold Spring Harbor Laboratory, Cold Spring Harbor, N.Y.). Other isolation methods known and used in the art may also be employed.

To produce recombinant Oxidoreductase polypeptides or peptides, DNA sequences encoding the polypeptides or peptides can be cloned into a suitable vector for expression in intact host cells or in cell-free translation systems as described above (see also J. Sambrook et al., 1989, *Molecular Cloning: A Laboratory Manual*, 2nd edition, Cold Spring Harbor Laboratory Press, Cold Spring Harbor, N.Y.). DNA sequences can be optimized, if desired, for more efficient expression in a given host organism. For example, codons can be altered to conform to the preferred codon usage in a given host cell or cell-free translation system using techniques routinely practiced in the art.

For some purposes, it may be preferable to produce oxidoreductase peptides or polypeptides in a recombinant system wherein the peptides or polypeptides carry additional sequence tags to facilitate purification. Such markers include epitope tags and protein tags. Non-limiting examples of epitope tags include c-myc, haemagglutinin (HA), polyhistidine (6×-HIS), GLU-GLU, and DYKDDDDK (FLAG®; SEQ ID NO:5, SEQ ID NO:6) epitope tags. Non-limiting examples of protein tags include glutathione-S-transferase (GST), green fluorescent protein (GFP), and maltose binding protein (MBP).

Epitope and protein tags can be added to peptides by a number of established methods. For example, DNA sequences encoding epitope tags can be inserted into protein-coding sequences as oligonucleotides or as primers used in PCR amplification. As an alternative, protein-coding sequences can be cloned into specific vectors that create fusions with epitope tags; for example, pRSET vectors (Invitrogen Corp.). Similarly, protein tags can be added by cloning the coding sequence of a polypeptide or peptide into a vector that creates a fusion between the polypeptide or peptide and a protein tag of interest. Suitable vectors include, without limitation, the exemplary plasmids, pGEX (Amersham-Pharmacia Biotech, Inc.), pEGFP (CLONTECH Laboratories, Inc.), and pMAL™ (New England BioLabs, Inc.). Following expression, the epitope or protein tagged polypeptide or peptide can be purified from a crude lysate of the translation system or host cell by chromatography on an appropriate solid-phase matrix. In some cases, it may be preferable to remove the epitope or protein tag (i.e., via protease cleavage) following purification.

In various embodiments, the recombinant oxidoreductase polypeptides are secreted to the cell surface, retained in the cytoplasm of the host cells, or secreted into the growth media. In each case, the production of oxidoreductase polypeptides can be established using anti-ketoreductase antibodies, or catalytic assays. The cell-surface and cytoplasmic recombinant Oxidoreductase polypeptides can be isolated following cell lysis and extraction of cellular proteins, while the secreted recombinant oxidoreductase polypeptides can be isolated from the cell growth media by standard techniques (see I. M. Rosenberg (Ed.) 1996, *Protein Analysis and Purification: Benchtop Techniques*, Birkhauser, Boston, Cambridge, Mass.).

Methods to improve polypeptide production may include 1) the use of bacterial expressed fusion proteins comprising signal peptides or targeting sequences to promote secretion (Tessier et al., 1991, *Gene* 98:177-83; Garnier et al., 1995, *Biotechnology* 13:1101-4); 2) the use of serum-free and protein-free culture systems for economical polypeptide production (Zang et al., 1995, *Biotechnolog* 13:389-92); 3) the use of the eukaryotic regulated secretory pathway for increased production and harvesting efficiency (see Chen et al., 1995, *Biotechnology* 13:1191-97). Polypeptide production may also be optimized by the utilization of a specific vector, host cell, expression system, or production protocol, as described in detail herein.

Large-scale microbial protein production can be achieved using well-established methods (see, e.g., W. Crueger and A. Crueger, 1990, *Biotechnology: A Textbook of Industrial Microbiology* Sinauer Associates, Sunderland, Mass.; A. N. Glazer and H. Nikaido, 1995, *Microbial biotechnology: fundamentals of applied microbiology Freeman*, New York, N.Y.; C. M. Brown et al., 1987, *Introduction to Biotechnology: Basic Microbiolog*, Vol. 10, Blackwell, Oxford, UK). Methods for scaling-up baculovirus protein production can be found, for example, in R. L. Tom et al., 1995, *Methods Mol. Biol.* 39:203-24; R. L. Tom et al., 1995, *Appl. Microbiol. Biotechnol.* 44:53-8; S. A. Weiss, et al., 1995, *Methods Mol. Biol.* 39:79-95; and C. D. Richardson (Ed.) 1995, *Baculovirus Expression Protocols: Methods in Molecular Biology*, Vol. 39, Humana Press, Totowa, N.J. In additional, large-scale protein production services are commercially available from, e.g., PanVera Corp., Madison, Wis.; Oxford Expression Technologies, Oxford UK; BioXpress Laboratory, Athens, Ga.; and Recombinant Protein Expression Laboratory, Gainesville, Fla.

In general, large-scale microbial enzyme production systems employ the following procedures. Screens are used to test enzyme activity, pH optimum, temperature optimum, secretion (downstream processing), and the ability to grow the organism in inexpensive large-scale fermentation systems (high population densities from inexpensive carbon and nitrogen feedstocks, e.g., corn syrup, molasses, soybean meal, gluten, etc.). Strain improvements are created by random mutagenesis and screening or directed genetic manipulation (e.g., in *Bacillus, Streptomyces, Aspergillus* and *Saccharomyces* strains). For example, mutant strains can provide 1) relief of repression (e.g., catabolite repression); 2) increased promoter strength; 3) higher affinity ribosome-binding sites; 4) higher efficiency of mRNA leader translation; 5) increased mRNA half life; 6) increased translation efficiency through altered codon usage; 7) improvement of secretion efficiency; and 8) increased gene dosage (i.e., via chromosomal amplification or plasmid amplification). Process improvements are implemented by screening feeding strategies (e.g., batch, fed-batch, continuous, or recycle), reactor configurations, stirring methods (e.g., via impeller, bubble, air lift, packed bed, solid state, or hollow fiber), pH control, foam, and temperature. Enzymes produced by exemplary large-scale microbial systems include various serine proteinases, Zn metalloproteinases, aspartic proteinases, isomerases, pectinases, lipases, α-amylase, cellases, and glucomylases.

The enzyme produced may also be purified by means known in the art, such as ion-exchange, hydrophobic, gel filtration, and affinity chromatography.

Keto-Reduction of Pyrrolotriazine Compounds

In one embodiment of the invention, starting materials in the subject process for preparing compounds according to formula Ib are the corresponding keto group-containing compounds represented by the formula IIb, i.e. 1-[4-(4-Halo-2-methyl-1H-indol-5-yloxy)-5-methyl-pyrrolo [2,1-f][1,2,4]triazin-6-yloxy]-propan-2-ones.

Formula IIb

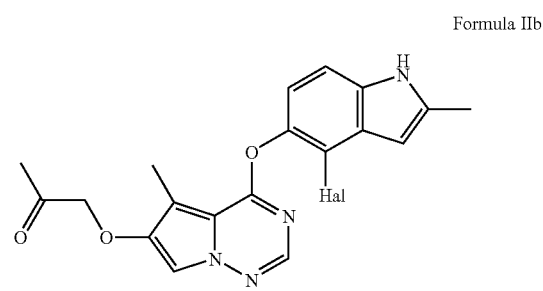

wherein Hal is defined above. One example is the compound of formula IIc.

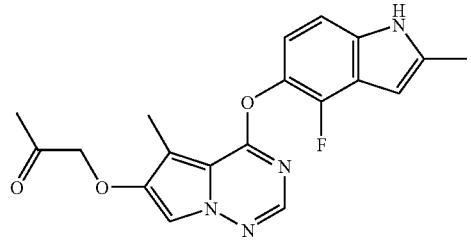

Formula IIc

The stereoselective reduction may produce alcohols of opposing enantiomerism, and in that regard particular enzymes and substrates may be used to produce the desired enantiomers. For example, an alcohol according to formula Ic*

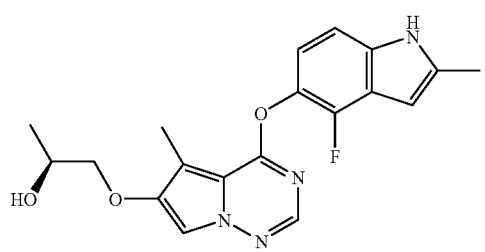

Formula Ic* may be formed from an enzymatic reaction conducted using a ketoreductase pRHBR7.0 with substrate IIb, which is described herein. Accordingly, the oxidoreductase enzymes of the invention may be used with a substrate to produce the desired enantiomer.

The substrate compounds represented by formula II or formula Ia (i.e, IIb or IIc) can be prepared by techniques described in the literature and known to those of ordinary skill in the art. A typical process for forming the compounds represented by formula II is disclosed below.

Scheme 1-Preparation of a Compound of Formula IIc

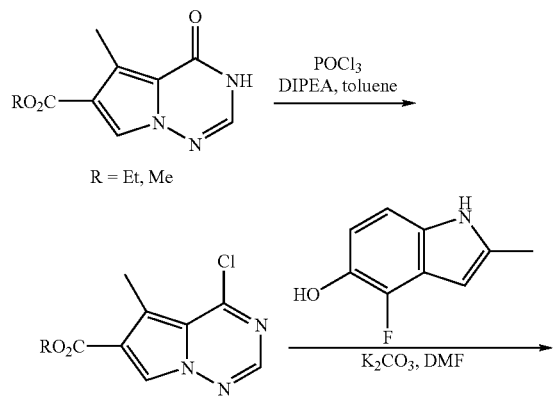

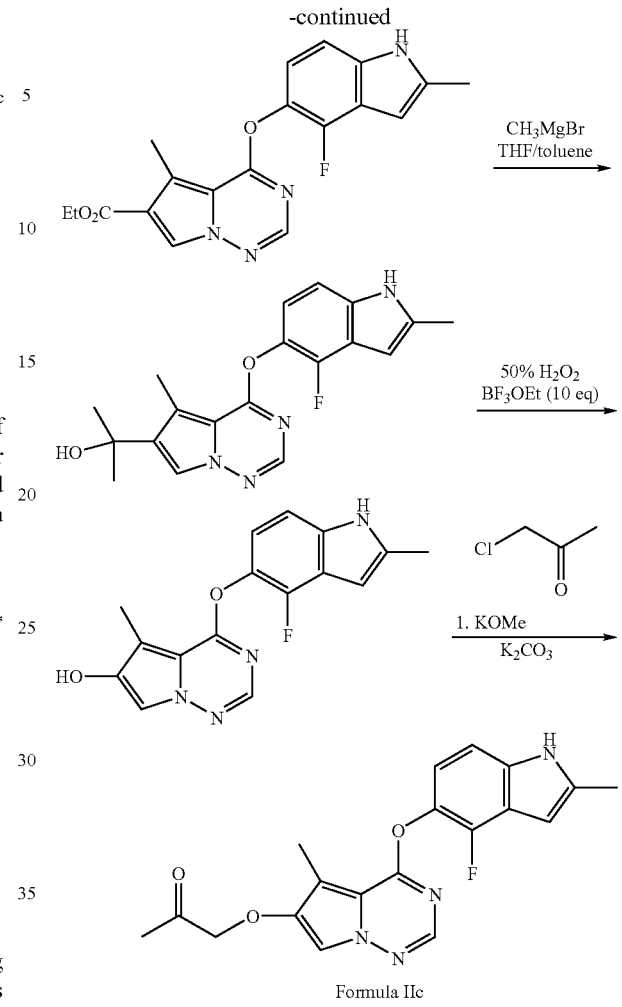

Formula IIc

The stereoselective reduction of 1-[4-(4-fluoro-2-methyl-1H-indol-5-yloxy)-5-methyl-pyrrolo[2,1-f][1,2,4]triazin-6-yloxy]-propan-2-one represented by formula IIc above to form 1-[4-(4-fluoro-2-methyl-1H-indol-5-yloxy)-5-methyl-pyrrolo[2,1-f][1,2,4]triazin-6-yloxy]-propan-2-ol represented by formula Ic is carried out in accordance with the invention by reaction with an oxidoreductase enzyme, or preferably, a microorganism that supplies an oxidoreductase enzyme capable of catalyzing the enzymatic reduction of the ketones represented by formula II. The cells of the microorganism may be in the form of intact wet cells or dried cells such as lyophilized, spray-dried or heat-dried cells, or in the form of treated cell material such as ruptured cell or cell extracts. While a large and varied number of microorganisms are known to supply some form of oxidoreductase, it has been found in accordance with the invention that only selected species of *Rhodococcus, Flavobacterium, Saccharothrix*, and *Pichia* catalyze the reduction of the compound represented by formula II to form the desired compound represented by formula I in high quantitative and enantiomeric yield. These species are *Rhodococcus australis* (ATCC 35215), *Pichia angusta* (ATCC 58401) ketoreductase expressed in *Eherichia coli, Flavobacterium fuscum*, (ATCC 25310) *Saccharothrix aerocolonigenes* (ATCC 39243), and *Pichia methanolica* (ATCC 56508). The term "ATCC" as used herein refers to the accession number of the depository for the particular organism, i.e. the American Type Culture Collection, 12301 Parklawn Drive, Rockville, Md. 20852.

The enzymatic reduction method of the invention may be carried out subsequent to the fermentation of the microorganism employed, i.e. as a two-stage fermentation and reduction, or concurrently therewith, i.e. as a single-stage or in situ fermentation and reduction. In the latter, the microorganism may be grown in an appropriate medium, especially one containing nitrogen and carbon sources, until sufficient growth is realized and then a compound selected from those compounds represented by formula II is added thereto. The enzymatic reduction is thereafter continued until virtually complete conversion of the compound represented by formula II is attained.

In the two-stage methodology, the microorganism is initially grown in a suitable medium as described above until it exhibits a predetermined level of enzymatic activity at which point the cells are harvested by conventional separation techniques and microbial cell suspensions prepared therefrom containing appropriate buffering agents and the like. Suitable buffering agents include phosphate buffers, particularly potassium phosphate buffer, tris-HCl, sodium acetate and the like. Water may also be used to prepare suspensions of microbial cells. The compound represented by formula II is then added thereto and the enzymatic reduction continued until the conversion is virtually complete. In either instance, the appropriate growth medium will include, as previously stated, sources of carbon and nitrogen and trace elements. Inducers may be added as well. The term "inducer" means any compound initiating or enhancing the desired enzymatic, i.e. oxidoreductase, activity within the cell to produce the desired product. 1-[4-(4-Fluoro-2-methyl-1H-indol-5-yloxy)-5-methyl-pyrrolo [2,1-f][1,2,4]triazin-6-yloxy]-propan-2-one represented by formula IIc would be considered an inducer, particularly when added in small quantities during the growth of the microorganism.

Suitable carbon sources for the medium may include sugars, such as maltose, lactose, glucose, fructose, sorbitol, sucrose, starch, mannitol, and the like, organic acids and their salts such as sodium acetate, sodium citrate and the like, amino acids and their salts, such as sodium glutamate and the like, and alcohols, such as ethanol, propanol, glycerol, propylene glycol and the like. Suitable nitrogen sources may include N-Z amine A, corn steep liquor, soy bean meal, beef extracts, yeast extracts, molasses, baker's yeast, tryptone, nutrisoy, peptone, yeastamin, sodium nitrate, ammonium sulfate and the like. Suitable salts may include phosphates, sodium, potassium, magnesium, and calcium salts. Suitable trace elements may include cobalt, nickel, iron, and manganese. The appropriate media utilized in accordance with the invention may include a plurality of constituents selected from any of these categories. Representative preferred media include aqueous media containing the following, in weight percent:

|  | Ingredient | Weight Percent |
|---|---|---|
| No. 1 | Malt Extract | 1% |
| pH 7.0 | Yeast Extract | 1% |
|  | Peptone | 1% |
|  | Glucose | 2% |
| No. 2 | Malt Extract | 1% |
| pH 7.0 | Yeast Extract | 1% |
|  | Peptone | 0.3% |
|  | Glucose | 4% |

-continued

|  | Ingredient | Weight Percent |
|---|---|---|
| No. 3 | Malt Extract | 1% |
| pH 7.0 | Yeast Extract | 1% |
|  | Peptone | 0.3% |
|  | Glucose | 2% |
| No. 4 | Malt Extract | 1% |
| pH 7.0 | Yeast Extract | 1% |
|  | Peptone | 0.3% |
|  | Sodium Succinate | 2% |

The pH given above for the media is post-sterilization. Before sterilization, the pH is preferably adjusted to from about 6 to 8, most preferably about pH 6.5. The media are then sterilized, for example, by heating at a temperature of about 121° C. for 30 minutes. Following sterilization, the media are adjusted to pH 6.5 to 7.5, most preferably about pH 7.0. During microbial growth and the reduction process, the pH is maintained at between about 4.0 and 9.0, preferably between about pH 6.0 and 8.0. An appropriate base or acidic salt from among the constituents named above can conveniently be utilized for adjustment of the pH.

The temperature of the reaction mixture is a measure of the heat energy available for the reduction process, and for this reason, a suitable temperature should be maintained to ensure that there is sufficient energy available for the process to go to completion. A suitable temperature range for the process of the invention is in the range of from about 15° C. to about 60° C., preferably from about 25° C. to about 40° C. Pressure is not known to be critical for the practice of the process of the invention and for convenience atmospheric pressure is typically maintained.

The process of the invention is preferably carried out under aerobic conditions. Agitation and aeration of the reaction mixture is also beneficial to the subject process in that it affects the amount of oxygen available for the biotransformation. The process is advantageously carried out, for example, in shake-flask cultures or fermentor tanks during the growth of the microorganisms in a single-stage or two-stage process as described above. Agitation in the range of about 50 to 1000 RPM is preferred, with about 50 to 500 RPM being most preferred. Aeration of about 0.1 to 10 volumes of air per volume of media per minute (v/Vt.) is preferred, with aeration of about 1 volume per volume of media per minute being particularly preferred.

Complete conversion of the compound represented by formula II may require, for example, from about 4 to 48 hours, typically from about 4 to 24 hours, measured from the time of addition of the compound represented by formula II to the media. It is preferred that the media be aqueous based, although an organic liquid or a miscible or immiscible, i.e. biphasic, organic/aqueous liquid mixture may be utilized as well.

The stereoselective enzymatic reduction process of the invention may be carried out using a co-factor such as nicotinamide adenine dinucleotide (NADH), or nicotinamide adenine dinucleotide phosphate (NADPH) especially when an isolated enzyme would be utilized. NADH or NADPH, for example, may thereafter be regenerated and reused. A further enzyme that regenerates the NADH in situ may be employed such as formate dehydrogenase or glucose dehydrogenase. Similarly, NADPH may be regenerated by glucose dehydrogenase. Suitable hydrogen donors include molecular hydrogen, a formate (e.g. an alkali metal or ammonium formate), glucose, a hypophosphite or an electrochemical reduction in the presence of a viologen, for example methyl viologen. It is also possible to regenerate NADH without further enzymes using, for example, ethanol or formate.

It is further preferred to add the compound of formula II to the reaction media so that it is up to about 100 g/L, for example based on weight per liter of the reaction medium; the desired amount may also be expressed as from about 0.2% to about 5% by weight, based on the combined weight of starting compound and media. The inoculum of microorganism relative to the amount of starting material is sufficient to provide for the enzymatic reduction of the compound represented by formula II with the times described above, generally from about 5 wt. % to about 30 wt. % cells concentration. Utilizing the preferred reaction parameters described above with the microorganisms given will provide a reaction yield of greater than 70%, optimally in excess of 99% and, an enantiomeric purity greater than 93%, optimally in excess of 99% of the desired enantiomer of the compound represented by formula I. The product of the reduction process of the invention, i.e. the compounds represented by formula I may be recovered by any suitable methods for isolation and/or purification, e.g. methodologies such as extraction, distillation, crystallization, column chromatography and the like.

It is understood that various other embodiments and modifications in the practice of the invention will be apparent to, and can be readily made by, those of ordinary skill in the art without departing form the scope and spirit of the invention as described above.

EXAMPLE 1

1-[4-(4-Fluoro-2-methyl-1H-indol-5-yloxy)-5-methyl-pyrrolo[2,1-f][1,2,4]triazin-6-yloxy]-propan-2-one

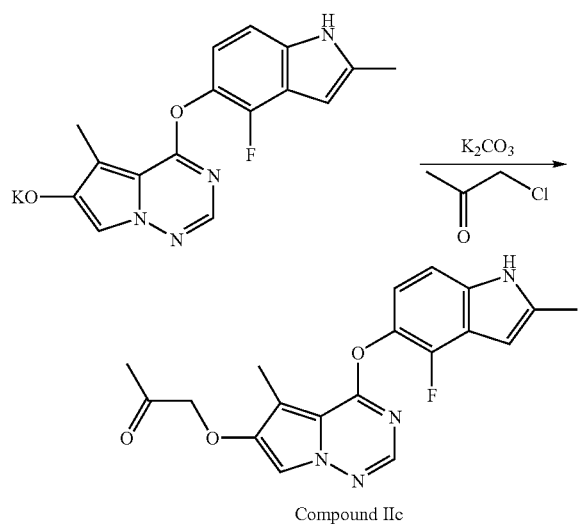

Compound IIc

Preparation: A solution of potassium 4-(4-fluoro-2-methyl-1H-indol-5-yloxy)-5-methyl-pyrrolo[2,1-f][1,2,4]triazin-6-olate (126.13 mmoles; 50.00 g) in dimethylformamide (200 mL), prepared from 4-(4-fluoro-2-methyl-1H-indol-5-yloxy)-5-methyl-pyrrolo[2,1-f][1,2,4]triazin-6-ol with one equivalent of 25% potassium methoxide in methanol, was stirred at room temperature for 1-2 h. This solution was added slowly over 2 h to a mixture of chloroacetone (214.42 mmoles; 17.40 mL), potassium carbonate (63.06 mmoles; 8.80 g) and dimethylformamide (100 mL). Stirring continued for another 15 h at room temperature and 300 mL of water was added slowly over 20 minutes, ~10° C. exotherm was observed. The slurry was cooled to 15° C. and filtered after 1 h. The filter cake was washed with 200 mL of 2:1 water-DMF mixture followed by 200 mL water. The wet cake was dried at 50° C. in a vacuum oven for 16 h to provide the ketone product (44.22 g; 95.18% yield) as a solid.

Recrystallization: The dry cake was slurried in 440 mL of tetrahydrofuran and heated to 50° C. 660 mL of water was added slowly over 1 h and heating continued at the same temperature for another 2 h. The slurry was cooled to 15° C. over 1 h and stirred for 2 h, then filtered. The filter cake was washed with 300 mL of water-tetrahydrofuran (2:1) mixture and dried at 50° C. in a vacuum oven for 16 h to provide 1-[4-(4-fluoro-2-methyl-1H-indol-5-yloxy)-5-methyl-pyrrolo[2,1-f][1,2,4]triazin-6-yloxy]-propan-2-one (40.1 g; 86.3% yield) as a solid with a purity of 99.1% as judged by HPLC. MS: (M+H)$^+$=369.

EXAMPLE 6

Alternate

Preparation: A solution of potassium 4-(4-fluoro-2-methyl-1H-indol-5-yloxy)-5-methyl-pyrrolo[2,1-f][1,2,4]triazin-6-olate (126.13 mmoles; 50.00 g) in dimethylformamide[1] (200 mL), prepared from 4-(4-fluoro-2-methyl-1H-indol-5-yloxy)-5-methyl-pyrrolo[2,1-f][1,2,4]triazin-6-ol with one equivalent of 25% potassium methoxide in methanol, was prepared and stirred at room temperature for 1-2 h. Chloroacetone (151.35 mmoles; 12.28 mL) was charged, a 5° C. exotherm was observed and stirring continued at room temperature for 1 h. Additional chloroacetone (63.06 mmoles; 5.12 mL) along with potassium carbonate[3] (63.06 mmoles; 8.80 g) was added and stirring continued for another 15 h at room temperature. About 300 mL of water was added slowly over 20 minutes, ~10° C. exotherm was observed. The slurry was cooled to 15° C. and filtered after 1 h. The filter cake was washed with 200 mL of 2:1 water-DMF mixture followed by 200 mL water. The wet cake was dried at 50° C. in a vacuum oven for 16 h to provide the ketone product (45 g; 96.85% yield) as a solid.

Recrystallization: The dry cake was slurried in 450 mL of tetrahydrofuran[4] and heated to around 50° C. Then 675 mL of water was added slowly over 1 h and heating continued at the same temperature for another 2 h. The slurry was cooled to 15° C. over 1 h and stirred for 2 h, then filtered. The filter cake was washed with 300 mL of water-tetrahydrofuran (2:1) mixture and dried at 50° C. in a vacuum oven for 16 h to provide 1-[4-(4-fluoro-2-methyl-1H-indol-5-yloxy)-5-methyl-pyrrolo[2,1-f][1,2,4]triazin-6-yloxy]-propan-2-one (37.6 g; 81% yield) as a solid with a purity of 99.1% as judged by HPLC. MS: (M+H)$^+$=369.

[1] This reaction also can be performed in acetonitrile solvent.
[2] Potassium ethoxide and sodium methoxide bases also gave similar results.
[3] Sodium carbonate, cesium carbonate and DBU bases also can be used.
[4] Recrystallization from acetone/methyl t-butylether mixture and methylenechloride alone also gave similar results.

EXAMPLE 2

Stereoselective Enzymatic Reduction: Use of Whole Cells—Single Stage Process

Various microbial cultures independently was inoculated into 100 mL of Medium 1 as noted above in a 500 mL flask and incubated at 28° C. and 200 RPM on a shaker for 22 hours. The pH of broth was adjusted to pH 7.0 with 1 M potassium phosphate buffer. Glucose was added to the cell broth at 25 mg/mL and 50 mg of 1-[4-(4-fluoro-2-methyl-1H-indol-5-yloxy)-5-methyl-pyrrolo[2,1-f][1,2,4]triazin-6-yloxy]-propan-2-one represented by represented by formula IIc was added thereto. The biotransformations (reductions) were carried out at 28° C. and 200 RPM on a shaker. At predetermined times, the 1 mL reaction mixtures were quenched with 4 mL of ethyl acetate. Two mL of the separated organic phase was evaporated to dryness under a stream of nitrogen and the residue taken up with 1 mL of acetonitrile, filtered through a 0.2 micron filter and analyzed by HPLC for 1-[4-(4-fluoro-2-methyl-1H-indol-5-yloxy)-5-methyl-pyrrolo[2,1-f][1,2,4]triazin-6-yloxy]-propan-2-ol represented by formula Ic. The results are summarized in Table 1 below.

HPLC Method: To determine the conversion of substrate to product

Column: YMC pack Pro C18, 50×4.6 mm, 3 µm, Waters
Solvent A (0.05% TFA in Water:Methanol 80:20)
Solvent B: (0.05% TFA in Acetonitrile:Methanol 80:20)
Start % B=50% B
End % B=60% B
Gradient Time=5 min
Wavelength=220 nm
Flow rate=1 ml/min
Temperature=room temperature
Stop Time=5 min
Retention Times

| Ketone (formula IIc) | 3.8 min |
|---|---|
| Alcohol (formula Ic) | 3 min |

HPLC Method: To determine the enantiomeric purity of the product

Column: Chiralpak AD-RH, 150×4.6 mm, 5 µ, Chiral Technologies Inc.
Solvent A: Heptane
Solvent B: (Heptane:isopropanol 50:50)
Isocratic 20% B
Flow rate=0.5 mg/ml
Temperature=ambient
Wavelength 1: 220 nm
Retention Times:

| Ketone | 17.8 min |
|---|---|
| Desired Alcohol | 20.8 min |
| Undesired alcohol, enantiomer of | 22.8 min |

TABLE 1

| Microbial Cultures | Yield (M %) | % Enantiomeric Excess |
|---|---|---|
| *Rhodococcus australis*, ATCC 35215 | 19 | >99 |
| rE. coli | 2 | 93 |
| (*Pichia angusta* ATCC 58401 ketoreductase) | | |
| *Flavobacterium fuscum*, ATCC 25310 | 12 | 89 |
| *Saccharothrix aerocolonigenes*, ATCC 39243 | 16 | 84 |
| *Pichia methanolica*, ATCC 56508 | 2 | 74 |

EXAMPLE 3

Cell Extracts Process

The substrate and the product for this Example were as described in Example 1. The two cultures of *Flavobacterium fuscum* (ATCC 25310) and *Saccharothrix aerocolonigenes* (ATCC 39243) were grown in both glucose medium (F7) and glycerol medium (using glycerol instead of glucose in F7). Cell suspension in buffer containing 50 mM potassium phosphate buffer, 10% glycerol, 2 mM DTT, 1 mM EDTA, and 1 mM PMSF (16 g cells in 100 mL of buffer). After homogenizing the mixture for 30 to 60 seconds, the cell extract was prepared by microfluidization of the homogenized cells. The cell extract was centrifuged at 18,000 rpm for 20 min. and supernatant was used in bioreduction.

Cell extracts of *S. aerocolonigenes* grown in both media gave 11% conversion. *F. fuscum* cell extracts gave 90% conversion and >99% enantiomeric purity of formula Ic (product I). Formula IIc (substrate II) was used at 1 g/L (in DMSO or DMF as solvent) input in the reduction process. The activity and selectivity was higher with NAD as co-factor than with NADP. The activity was also higher with glucose dehydrogenase (GDH) and glucose as co-factor regeneration system than with formate dehydrogenase (FDH) and sodium formate. Results are as shown in the Table 2 below.

TABLE 2

| Microorganism | Reaction Time (hrs) | Substrate Used (mg/mL) | Product M % Yield | Enantiomeric purity (%) |
|---|---|---|---|---|
| *Saccharothrix aerocolonigens* ATCC 39243 | 20 | 1.0 | 11 | >90 |
| | 32 | 2.0 | 8 | >90 |
| *Flavobacterium fuscum* ATCC 25310 | 2 | 1.0 | 95 | >99 |
| | 2 | 2.0 | 87 | >99 |
| | 2 | 5.0 | 72 | >99 |

EXAMPLE 4

Reduction Process using Recombinant *Escherichia coli*

A reductase (88,000 molecular weight with 29,000 subunit size molecular weight) from *Pichia angusta*, ATCC 58401 was purified and cloned in *Escherichia coli*. The recombinant strain also contained a gene for glucose-6-phosphate dehydrogenase. This rec. *Escherichia coil* cells were grown in a medium containing 2% yeastamine; 4% glycerol; 0.6% sodium phosphate, dibasic; 0.3% potassium phosphate, monobasic, 0.125% ammonium sulfate; 0.0246% magnesium sulfate, heptahydrate; 0.005% kanamycin adjusted to pH 7.2. Cells were grown in a 4-L flask containing 1 L medium at 30° C., 250 RPM for 24 hours. Cells were harvested and used in the reduction process at 1 g/L Formula IIc substrate input. After 24 hours reaction, Formula Ic was obtained in 12% yield with an e.e. of 93%. Cell extracts of rec. *Escherichia coli* expressing *Pichia angusta* keto reductase gave 21% yield and >99% e.e. for compound I. Glucose and glucose dehydrogenase were used to regenerate cofactor NADH required for this reduction.

Enzyme Purification and Sequencing

*Pichia angusta*, ATCC 58401 cells (2.088 kg) were obtained from a 50-L fermentation. Using a whole cell assay measuring conversion of 1 mg/ml 2-chloro-1-(3-chlorophenyl)ethanone to (S) 2-chloro-1-(3-chloro-phenyl)-ethanol, activity was highest 37 h after the start of the fermentation (72% conversion in 1 h with 80% ee). Activity when cells were harvested after 48 h was 32% conversion in 1 h with 85% ee. Purification of the *Pichia angusta*, ATCC 58401 ketoreductase was carried out to obtain amino acid sequences necessary for Polymerase Chain Reaction (PCR) amplification of the corresponding gene. During initial purification attempts the activity was not stable, despite the addition of yeast protease inhibitor cocktail, 10% glycerol and 1 mM dithiothreitol. Of various additives tried for stabilization, only NADP and NADPH were effective (NAD was not effective). Therefore 0.5 mM NADP was added to column buffers. The ketoreductase from *Pichia angusta*, ATCC 58401 was purified 112-fold from an extract using Phenylsepharose, Q-Sepharose and Sephacryl S-100. FPLC with a unoQ column was used as a final step to obtain a single band on an SDS gel that was blotted to PVDF for sequencing. The subunit molecular weight determined with an Agilent Bioanalyzer 2100 Protein 200 Labchip was 27 kd.

An N-terminal sequence (H2N-DKLPTEAPQLP) was obtained which showed sequence homology with sorbitol dehydrogenase from *Candida albicans*. A tryptic digest gave several peaks which contained an estimated 50-100 pmoles of peptide and sequences of two of the internal peptides (AIMNTNLDGVYYCAK and SLAMEWVGFAR) were obtained. These sequences also showed homology with dehydrogenases in the data bases.

Cloning

Degenerate primers for the N-terminal and internal sequences were used in PCR reactions to clone 400 and 600 base pair (bp) fragments of the ketoreductase gene from *Pichia angusta*, ATCC 58401 DNA. The 400 bp fragment was used to prepare a digoxigenin-labelled probe which bound to a 4 kilobase (kb) band from a XhoI digest of *Pichia angusta*, ATCC 58401 chromosomal DNA. A library was prepared in *E. coli* containing DNA from the 4 kb region of the XhoI digest ligated to the pZErO-2 vector, and the probe was used to identify *E. coli* colonies carrying the homologous sequence. Sequencing of the plasmid prepared from one of the hybridizing colonies showed that the insert contained an open reading frame homologous to known ketoreductases and that the sequences corresponding to the amino terminal and two internal peptides of the purified enzyme were present (SEQ ID NO:1). Primers that included NdeI and SmaI sites before the start and stop sites of the insert, respectively, were used to amplify the ketoreductase gene. The amplified fragment was ligated into pBMS2000 for expression in *E. coli* BL21 Star(DE3) under the control of the tac promoter. After growth of the cells and induction with 1 mM isopropyl □-D-thiogalactoside (IPTG), a sonicated extract was prepared that contained a predominant 27 kd protein. In an activity assay, the extract gave complete conversion of 2-chloro-1-(3-chlorophenyl)ethanone to (S) 2-chloro-1-(3-chloro-phenyl)-ethanol with 100% ee.

Molecular Weight of Native Ketoreductase

The molecular weight of the expressed ketoreductase in the extract was estimated as 88,094 by Superdex-200 gel filtration chromatography. The peak fraction from the column contained a single 27 kd subunit when analyzed with a Protein 200 Labchip (SEQ ID NO:3, lanes 5 and 10). From the amino acid composition derived from the gene sequence, the subunit molecular weight is 29,220, suggesting that the native enzyme is a trimer.

Expression of *Pichia Angusta*, ATCC 58401 and *Saccharomyces cerevisiae* glucose-6-phosphate dehydrogenase in *E. coli*

The ketoreductase was copied from the plasmid by PCR. SmaI and HindIII sites were added upstream of the promoter and a SmaI site was added at the 3' end via the primers. The ketoreductase gene was ligated at a SmaI site into pBMS2000-SCGD which contains a cloned *S. cerevisiae* glucose 6-phosphate dehydrogenase gene. Restriction digests with BamHI and NdeI were used to identify plasmids with the two genes in the same orientation, which was thought to be a desired situation for a higher transcription rate. One of the plasmids with the desired orientation was used to transform BL21Star(DE3) *E. coli* for expression. This strain was designated *E. coli*. The cells were induced with either 50 µM or 1 mM IPTG. Expression of both enzymes was 2 to 3-fold better at 1 mM IPTG. Sonicated extracts of the cells with either concentration of inducer converted Formula IIc compound 2 to Formula Ic compound 1 in buffer containing NADP and glucose 6-phosphate. The desired alcohol of Formula Ic was obtained with >99.9% e.e. The nucleic acid sequence of the gene from *Pichia angusta* (SEQ ID NO:1) and its amino acid sequence (SEQ ID NO:2) are shown below.

Sequence of Ketoreductase Gene.

Peptides from amino acid sequencing are underlined in bold.

```
    M N I I G N Y D K L P T E A P Q
  1 ATGAACATTATCGGAAATTACGACAAGCTACCAACCGAGGCTCCTCA
    A

L P S N V F S L F S L K G K V A
 49 TTGCCTTCCAACGTTTTCAGCCTGTTCTCCCTGAAAGGCAAGGTGGC
    C

S I T G G S T G I G L A V A E A
 97 AGCATTACTGGTGGCTCGACAGGAATTGGTCTGGCTGTGGCAGAAGC
    G

Y A Q A G A D V A I W Y N S T N
145 TATGCTCAGGCAGGCGCAGACGTGGCCATCTGGTACAACAGCACAAA
    C

A D H E A E R L S K T Y G I R A
193 GCTGACCACGAAGCTGAGAGGCTGTCCAAGACGTACGGGATCCGTGC
    C

K A Y K C A V G D F D Q V K A T
241 AAGGCTTACAAGTGCGCAGTGGGCGACTTTGACCAGGTCAAGGCCAC
    G

I D A I E S D F G T I H I F V A
289 ATCGATGCCATTGAGTCTGACTTTGGCACGATTCACATTTTTGTTGC
    A

N A G I G S Q S V P V I D A S L
337 AATGCGGGGATTGGCTCCCAATCGGTGCCTGTGATCGATGCGTCGCT
    G

E K Y R A I M N T N L D G V Y Y
385 GAAAAATACCGGGCAATCATGAACACGAATTTGGACGGCGTGTACTA
    C

C A K C V G P I F K K H G K G S
433 TGCGCCAAGTGCGTGGGTCCAATTTTCAAGAAGCACGGCAAGGGTTC
    C

F I I T T S Q A A H I V T A H V
481 TTTATCATCACCACCTCACAGGCAGCCCATATTGTCACGGCTCACGT
    G

W Q A A Y N A S K A A C I Q I A
529 TGGCAAGCGGCTTACAACGCCAGCAAGGCAGCGTGCATCCAGATTGC
    C
```

```
              -continued
     K  S  L  A  M  E  W  V  G  F  A  R  V  N  T  I
577 AAGAGTCTGGCAATGGAATGGGTCGGCTTCGCCCGTGTCAATACGAT
    C S  P  G  Y  I  V  T  P  I  S  K  D  V  P  N  E
625 TCTCCAGGGTACATTGTCACCCCTATCTCGAAAGATGTGCCTAACGA
    G E  K  V  K  W  C  T  L  I  P  M  G  R  E  G  L
673 GAGAAAGTCAAGTGGTGCACGTTGATCCCAATGGGCAGAGAGGGGCT
    T P  Q  E  L  V  G  A  Y  L  Y  F  A  S  D  A  S
721 CCTCAAGAGCTTGTGGGCGCATACCTGTACTTTGCGTCGGACGCCTC
    A T  F  T  T  G  A  D  L  I  I  D  G  G  Y  C  C
769 ACCTTCACCACCGGCGCTGACCTCATCATTGACGGTGGTTATTGCTG
    C

P  *
817 CCATAA
```

EXAMPLE 5

Reduction Process Using Commercially Available Ketoreductases

Four different (R)-specific ketoreductases commercially available from Biocatalytics, Inc. were evaluated for the reduction of Formula IIc to Formula Ic Glucose dehydrogenase and glucose were used to regenerate cofactor NADH required for this reduction. Three ketoreductases (KRED-A1B, KERD-A1C, KERD-A1D) gave the desired alcohol in reaction yield ranged from 47-75% with e.e. ranged from 99.3% to 100%.

In addition to the foregoing examples, it was determined that other oxidoreductase enzymes derived according to the following examples demonstrated some level of ketoreductase activity.

EXAMPLE 6

Heterologous Expression of Ketoreductase from *Flavobacterium fuscum* Conversion of Formula IIc ketone to Formula Ic Alcohol The ketoreductase protein from *Flavobacterium fuscum* was purified. An analysis of the DNA sequence encoding the 16S ribosomal RNA gene revealed that it was *Stenotrophomonas acidaminophila*.

The purified protein (molecular weight ~50 kiloDaltons) was submitted for amino acid sequencing and three distinct sequences were obtained. The N-terminal of the protein was determined to be MAEQFDVVIGAGPAGY. Two internal sequences were obtained from trypsin digest fragments of the purified protein: GQIIVDEH and AVAMVEPAGFVK. A comparison of these sequences to the GenBank protein database revealed high homology to the dihydrogenlipoamide dehydrogenase from *Xanthomonas campestris*. Synthetic oligonucleotide primers composed of nucleotide sequences capable of encoding the amino acid sequences derived from the purified protein were prepared and used for PCR reactions designed to amplify a portion of the target gene from *Flavobacterium fuscum* chromosomal DNA. Based on the similarity between our purified protein and the GenBank dihydrogenlipoamide dehydrogenase, the expect distance between the N-terminal and the first internal amino acid sequence shown above was ~900 bp. The distance between the N-terminal and the second internal sequence was expected to be ~1200 bp. After optimization of PCR conditions a single band was amplified from chromosomal DNA with each combination of PCR primers. As predicted, the amplified products were ~900 bp and ~1200 bp.

The ~1200 bp fragment was purified and ligated into a sequencing vector. The resulting plasmid (pCR4+1200VEGFR) was submitted for DNA sequencing. The completed sequence revealed a single open reading frame of 1215 bp encoding 405 amino acids. This open reading frame contained an exact match for both the N-terminal and the second internal amino acid sequences derived from the purified protein. Contained within this 1215 bp sequence, at a distance of 916 bp from the N-terminal, was an exact match of the 8 residue second internal amino acid sequence. This data indicates that a portion of the target gene encoding the purified protein had been successfully isolated.

Based upon the molecular weight of the purified protein, the expected size of the entire gene is ~1450 bp, indicating that ~15% of the target gene was not present in the 1215 bp PCR product. In order to isolate a DNA fragment containing the entire target gene, a library of *Flavobacterium fuscum* chromosomal DNA was prepared in a fosmid vector. Each fosmid construct was designed to contain a random 40 kilobase fragment of *Flavobacterium fuscum* chromosomal DNA (<1% of the entire genome). The recombinant fosmids were packaged in virus particles and used to transform *Escherichia coli*. Cells that had incorporated the fosmids were identified by the ability to form colonies in the presence of a selective antibiotic. The colonies were lysed and the fosmid DNA was transferred to a nylon filter. This filter was hybridized overnight in the presence of a chemoluminescently labeled sample of the original 1215 bp gene fragment. Those colonies that had incorporated a recombinant fosmid containing a 40 kilobase fragment that encompassed the 1215 bp ketoreductase region were identified by specific hybridization to the labeled probe. Eight positive colonies were identified. Each of these colonies was grown out in liquid medium and used to prepare recombinant fosmid DNA. Each fosmid preparation was tested for the ability to serve as a PCR template to reamplify the 1215 bp fragment using the ketoreductase N-terminal and internal primers. All of the fosmids amplified the correct fragment indicating that they contained the desired gene region. The recombinant fosmid DNA was digested with a variety of restriction endonucleases and the resulting fragments were transferred to a nylon filter. This filter was hybridized overnight with the labeled 1215 bp probe molecule. In each case a single band hybridized to the probe. The BamHI digest generated a single hybridizing fragment of ~6300 bp. This fragment was isolated and cloned into a sequencing vector. Using oligonucleotide primers based upon the DNA sequence of the initial 1215 bp PCR fragment, the regions of DNA surrounding the previously identified ketoreductase gene sequences were determined. The resulting DNA sequence indicated that the entire target gene had been successfully isolated. The VEGFR-KR gene (shown below) was 1425 bp and encoded a 474 amino acid protein (shown below) with a predicted molecular weight of 49,908 Daltons, matching the protein. This data, in conjunction with the presence of all three amino acid sequences found in the purified *Flavobacterium fuscum* protein indicates conclusively the gene encoding the purified protein had been isolated. The nucleic acid DNA sequence as well as the amino acid sequence of the isolated gene are shown below as SEQ ID NO: 3 and 4.

```
SEQ ID NO:3. Nucleic acid sequence of gene cloned
from Flavobacterium fuscum
(start)ATGGCTGAACAATTCGACGTCGTCGTCATCGGTGCCGGCCCGG
CCGGCTACCATGCCGCCATCCGCGCTGCCCAGCTGGGCTTGAAGACCGCC
TGCATCGATGCCGCGCTGGGCAAGGACGGCAAGCCGGCCCTGGGCGGCAC
CTGCCTGCGCGTGGGCTGCATCCCGTCCAAGGCGCTGCTGGATTCCTCGC
GCCAGTTCTGGAACATGGGCCACATCTTCGGCGAGCACGGCATCAGCTTC
GACAATGCCGGCATCGACGTGGAAAAGATGGTTGGCCGCAAGGACGCCAT
CGTCAAGCAGTTCACCGGCGGCATCGCGATGCTGTTCAAGGCCAACAAGG
TTGCCACCTACTACGGCTTCGGCCAGCTGCAGGCCGGCAATGTGGTCACC
GTGACCCAGCACGATGTTCGGTGGTTGAGCTCAAGGGCACCAACGTCAT
CATCGCCGCCGGCTCGGACTCGATCGAGCTGCCGTTTGCCAAGTTCGACG
GCAAGCACATCGTCGACAACGTCGGCGCGCTGGATTTCACCGAGACCCCG
AAGCGCCTGGGCGTGATCGGTGCCGGCGTGATCGGCCTGGAGCTGGGCTC
GGTCTGGAAGCGTCTGGGTTCGGAAGTCACCATCCTGGAAGCCGCGCCGA
ACTTCCTGGCCGCTGCCGACGCCGAAGTGGCCAAGCTGGCCGCGCGTGAA
TTCAAGAAGCAGGGCCTGGACATCAAGCTCGGCGCCAAGCTGGCCAAGGC
CGAAGTGGTCGGCGACGAAGTCGTGCTGACCTACAACGACGCCAATGGCG
AGCAGACCCTGACCGTGGACAAGCTGCTGGTGGCCGTCGGCCGCAAGGCC
GCCTCCAAGGGCCTGCTGGGCGAAGGCTGCCAGGTCAAGCTCAACGAGCG
TGGCCAGATCATCGTTGACGAGCACTGCCACACCGGCGTGGACGGCGTCT
GGGCCGTGGGTGACTGCGTGCGCGGGCCGATGCTGGCGCACAAGGGCTTC
GAGGAAGGCATCGCGGTGGCCGAACTGATCGCCGGCCTGCCGGGTCACGT
CAACTTCGACACCATCCCGTGGGTGATCTACACCGAGCCGGAGCTGGCCT
GGGTCGGCAAGACCGAACAGCAGCTCAAGGACGAGGGCATCCCGTACAAG
GCCGGCAGCTTCCCGTTCGCCGCCAACGGCCGTGCCGTGGCCGATGGTCGA
GCCGGCCGGTTTCGTCAAGGTCCTGGCCCACGCCGAGACCGACCGCGTGC
TCGGCATGCACCTGGTTGGCGCCAATGTCTCCGAGCTGGTGCACGAAGGT
GTGCTGACCATGGAGTTCAGCGGCTCGGCCGATGACCTGGCACGCATCTG
CCACGCCCACCCGTCGCTGTCGGAAGTGATTCACGACGCGGCGATGGCGG
TGAGCAAGCGCGCCATCCACAAGACCAACTGA(stop)

SEQ ID NO:4. Amino acid sequence encoded by
cloned gene
(matches to purified protein noted)
MAEQFDVVVI GAGPAGYHAA IRAAQLGLKT ACIDAALGKD
GKPALGGTCL RVGCIPSKAL LDSSRQFWNM GHIFGEHGIS
FDNAGIDVEK MVGRKDAIVK QFTGGIAMLF KANKVATYYG
FGQLQAGNVV TVTQHDGSVV ELKGTNVIIA AGSDSIELPF
AKFDGKHIVD NVGALDFTET PKRLGVIGAG VIGLELGSVW
KRLGSEVTIL EAAPNFLAAA DAEVAKLAAR EFKKQGLDIK
LGAKLAKAEV VGDEVVLTYN DANGEQTLTV DKLLVAVGRK
AASKGLLGEG CQVKLNERGQ IIVDEHCHTG VDGVWAVGDC
VRGPMLAHKG FEEGIAVAEL IAGLPGHVNF DTIPWVIYTE
PELAWVGKTE QQLKDEGIPY KAGSFPFAAN GRAVAMVEPA
GFVKVLAHAE TDRVLGMHLV GANVSELVHE GVLTMEFSGS
ADDLARICHA HPSLSEVIHD AAMAVSKRAI HKTN
```

A new set of oligonucleotide PCR primers were prepared to amplify the cloned gene while adding an NdeI restriction endonuclease cut site (CATATG) at the initiation codon and adding a BamHI cut site immediately downstream of the TGA terminator codon. This PCR reaction successfully amplified the modified ketoreductase gene from the isolated 6300 bp BamHI library fragment. The modified ketoreductase PCR fragment was digested with NdeI and BamHI and inserted into expression vector pBMS2004 (also cut with NdeI and BamHI), forming pBMS2004+VEGFRmod. This ligation reaction was used to transform E. coli and the correct construct was verified by PCR of the insert as well as diagnostic restriction digests of the recombinant plasmid pBMS2004+modified ketoreductase was used to transform the E. coli strain BL21.

The expression transformant, BL21/pBMS2004+VEGFR-mod, was grown in MT5-mod2 medium (2% Quest HyPea, 1.85% Tastone154, 4% glycerol, 0.6% $Na_2PO_4$, 0.125% $(NH_4)_2SO_4$, 0.04% UCON, supplemented with 50 μg/ml kanamycin) at 30 degrees until $OD_{600}$ ~0.9. At that point cultures were induced with isopropylthiogalactoside (IPTG) at either 1.0 mM, 0.2 mM, or 0.05 mM. Cell pellets were collected immediately before induction as well as 1, 3, or 20 hours post-induction. A parallel culture of untransformed BL21 served as a negative control. Protein samples from the expression cultures were prepared. Separate SDS/PAGE gels were run containing either the total cellular protein from each sample, or just the soluble protein fraction. A protein molecular weight standard was run in an adjacent lane. In each case the highly overexpressed heterologous protein has a molecular weight of ~50 kD, matching that of the protein purified from Flavobacterium fuscum as well as the predicted molecular weight based on the encoded amino acid sequence of the cloned gene.

Cells and extracts prepared from recombinant Escherichia coli gave conversion of Compound 2 to Compound 1.

EXAMPLE 7

Enzymatic Conversion of Formula IIc to Alternative Alcohol Enantiomer (Compound Ic*)

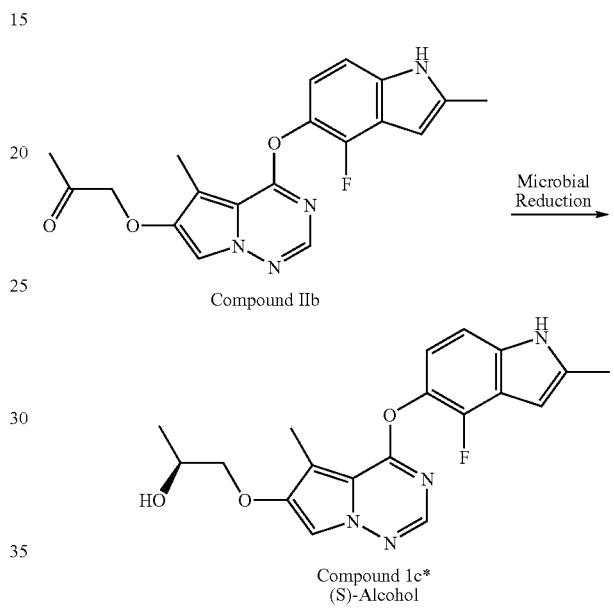

Compound IIb

Compound Ic*
(S)-Alcohol

Various microbial cultures (Table 4) were independently inoculated into 100 mL of Medium 1 as noted above in a 500 mL flask and incubated at 28° C. and 200 RPM on a shaker for 22 hours. The pH of broth was adjusted to pH 7.0 with 1 M potassium phosphate buffer. Glucose was added to the cell broth at 25 mg/mL and 50 mg of 1-[4-(4-fluoro-2-methyl-1H-indol-5-yloxy)-5-methyl-pyrrolo[2,1-f][1,2,4]triazin-6-yloxy]-propan-2-one represented by represented by formula II was added thereto. The biotransformations (reductions) were carried out at 28° C. and 200 RPM on a shaker. At predetermined times, the 1 mL reaction mixtures were quenched with 4 mL of ethyl acetate. Two mL of the separated organic phase was evaporated to dryness under a stream of nitrogen and the residue taken up with 1 mL of acetonitrile, filtered through a 0.2 micron filter and analyzed by HPLC for compound 3 (formula Ic*). The results are summarized in Table 1 below.

HPLC Method: To determine the conversion of substrate to product
Column: YMC pack Pro C18, 50×4.6 mm, 3 μm, Waters
Solvent A (0.05% TFA in Water:Methanol 80:20)
Solvent B: (0.05% TFA in Acetonitrile:Methanol 80:20)
Start % B=50% B
End % B=60% B
Gradient Time=5 min
Wavelength=220 nm
Flow rate=1 ml/min
Temperature=room temperature
Stop Time=5 min Retention Times

| | | |
|---|---|---|
| Formula IIc | 3.8 min | |
| Alcohol | 3 min | |

HPLC Method: To determine the enantiomeric purity of the product
Column: Chiralpak AD-RH, 150×4.6 mm, 5μ, Chiral Technologies Inc.
Solvent A: Heptane
Solvent B: (Heptane:isopropanol 50:50)
Isocratic 20% B
Flow rate=0.5 mg/ml
Temperature=ambient
Wavelength 1: 220 nm
Retention Times:

| | | |
|---|---|---|
| Formula IIc | 17.8 min | |
| Formula Ic | 20.8 min | |
| Alternative alcohol, | 22.8 min | |

(Formula III Enantiomer of Compound 1)

TABLE 4

Cultures Producing Alternative Alcohol Enantiomer (Compound 1c)

| Culture | Compound Ic Yield (M %) | Compound Ic % ee |
|---|---|---|
| Candida boidini (ATCC 26175) | 75.4 | 100 |
| Candida famata (ATCC 26418) | 98.6 | 100 |
| Candida kefyr (ATCC 748) | 86.4 | 100 |
| Hansenula polymorpha (ATCC 26012) | 77.2 | 100 |
| Hansenula polymorpha (ATCC13896) | 96.5 | 100 |
| Rhodococcus erythropolis (ATCC 25544) | 87.1 | 100 |
| Recombinant Cultures | | |
| Recombinant E. coli | 38.4 | 100 |
| Escherichia coli JM110(pBMS2000-PPFDH-SHBR) | 60.6 | 100 |
| Escherichia coli JM110(pBMS2000-SCGD-RHBR) | 39.5 | 100 |

(R)-1-(4-(4-fluoro-2-methyl-1H-indol-5-yloxy)-5-methylpyrrolo[1,2-f][1,2,4]triazin-6-yloxy)propan-2-ol

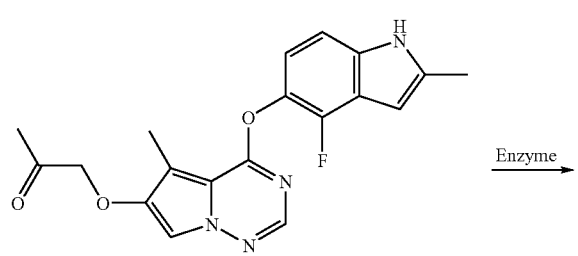

Enzyme →

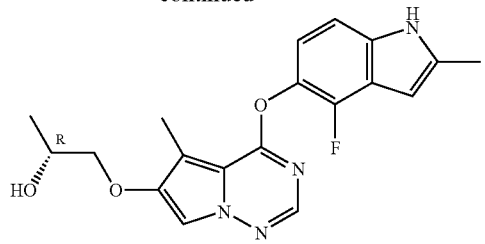

The reaction mixture from enzymatic reduction (with 50 g ketone input) was diluted with 400 mL 2-methyl tetrahydrofuran and 100 mL tetrahydrofuran and stirred at 20° C. for 2 h. Phases were separated and organic phase washed with 15 wt/vol % aqueous sodium chloride solution. The organic phase was filtered and concentrated at atmospheric pressure to a minimum agitation volume (~250 mL). Tetrahydrofuran (450 mL) was charged and concentrated again to minimum agitation volume. This process was repeated until the amount of residual 2-methyl tetrahydrofuran is below 5 vol/vol %. The mixture was diluted to 300 mL volume with tetrahydrofuran and heated to around 60° C. Heptane (500 mL) was added slowly over 2 h with seeding when around 100 mL of heptane was added. Stirring continued at the same temperature for another 2 h. The mixture was slowly cooled to 20° C. over 2 h and stirred for 16 h. The slurry was filtered and the filter cake was washed with 200 mL heptane. The wet cake was dried at 50° C. in a vacuum oven for 16 h to provide (R)-1-(4-(4-fluoro-2-methyl-1H-indol-5-yloxy)-5-methylpyrrolo[1,2-f][1,2,4]triazin-6-yloxy)propan-2-ol (45.13 g; 89.77% yield) as a solid with a purity of 98.92% as judged by HPLC. MS: (M+H)$^+$=371.

EXAMPLE 8

Purification of Reductase from *Pseudomonas putida* and Cloning of Ketoreductase in *Escherichia coli* to produce *Escherichia coli* JM110(pBMS2000-PPFDH-SHBR)

Growth of *Pseudomonas putida* was carried out in a 4-L flask containing 1 L of medium. The culture was grown in F7 medium (10 g/L yeast extract, 10 g/L malt extract, 1 g/L peptone and 20 g/L glucose, pH7). The flask was inoculated with 5% inoculum obtained from a 24-hour flask grown culture with F-7 medium. The cells were harvested after 48 hr growth at 28° C. and 150 RPM. Approximately 12 g of cells were obtained, which was stored at −70° C.

A. Purification of Ketoreductase
*Pseudomonas putida* cells were suspended at 10% in 500 ml of buffer A (10 mM phosphate buffer, pH 6.1 containing 10% glycerol, 1 mM DTT, 1 mM EDTA). The cell suspension was disintegrated by repeated passage through microfluidzer at 12,000 psi. The disintegrated cells was centrifuged at 14,000 rpm for 15 min at 4° C., and collected the supernatant containing the activity which was refer to as cell extracts.
Cell extracts was fractionated by solid ammonium sulfate as 0-30% saturation, 30-50% saturation and 50-80% saturation. The pellet obtained by 50-80% saturation was then solubulized in the buffer A and was loaded on to Sephacryl S-200 gel-filtration column (84×2.5 cm column). Fraction of 8 ml (12 min/fraction) were collected. Fractions (33-35) containing the activity were pooled and loaded on to a 5 ml Blue-gel (affinity column)column. The column was washed with 40 ml of buffer A. Elution of the enzyme was carried out by increasing the concentration of NAD (10 mM NAD in Buffer A). The fraction (eluted with 2 mM NAD) containing the activity was concentrated by Amicon concentrator (YM10) and was loaded onto the Sephadex-75 column. The enzyme had a molecular weight of 27 Kdaltons as judged by 12.5% SDS-PAGE and silver staining.

B. PVDF-Blotting and Sequencing of the Purified Protein

The purified protein was blotted on to a PVDF-membrane according to the manufactures instructions (Bio-Rad). The purified protein was stained with coomassie blue and the protein band was excised from the membrane. The excised protein was then sent out for sequencing to Argo Bioanalytica. The peptide sequences obtained from Argo Bioanalytica are as follows:

```
N-Terminal Sequence:   ANSRTALIIGASRGLG

Internal peptides:
Peptide 1:             NNDIGDLFMTNAVAPIR

Peptide 2:             AALNSMINSFFVEQQRPDLCVLAMHPG
```

A BLAST2 homology search using the above sequences showed significant regions of homology to short-chain dehydrogenases/reductases. For use in polymerase chain reaction (PCR), degenerate oligonucleotide primers were prepared based on the corresponding codons of the amino acids. The direction of the primers (i.e., sense and/or anti-sense) were determined using the likely location of the amino acid sequence within the protein by comparison to homologous dehydrogenases/reductases.

TABLE 5

| Primer name | Nucleotide sequence | Corresponds to (direction) |
|---|---|---|
| Oligo 424 | ACIGCIYTIATHATHGGIGC | TALIIGAS (sense) |
| Oligo 425 | TTYATGACIAAYGCIGTIGC | FMTNAVA (sense) |
| Oligo 426 | GCIACIGCRTTIGTCATRAA | FMTNAVA (anti-sense) |
| Oligo 427 | ACRAARAAOSWRTTDATCAT | MINSFFV (anti-sense) |

Standard nucleoside bases (adenosine, thymine, cytosine, and guanosine) are indicated by "A", "T", "C", or "G". "I"=inosine (replaces all four bases). Mixed bases are: "R" (A+G); "S" (C+G); "W" (A+T); "Y" (C+T). Amino acid abbreviations correspond to those designated by the International Union of Pure and Applied Chemistry (IUPAC). Combinations of sense and anti-sense primers were tried with the FailSafe series of PCR buffer and *P. putida* chromosomal DNA as template in 10 µL reactions. Amplification was carried out in a Hybaid PCR Express thermocycler using a five-stage "touchdown" PCR strategy:

| Stage 1 | Stage 2 | Stage 3 | Stage 4 | Stage 5 |
|---|---|---|---|---|
| 94° 1 min | 94° 30 sec | 94° 30 sec | 94° 30 sec | 72° 5 min |
|  | 55° 30 sec | 55°-->40° 30 sec | 40° 30 sec |  |
|  | 72° 30 sec | 72° 30 sec | 72° 30 sec |  |
| 1 cycle | 4 cycles | 20 cycles | 5 cycles |  |

Strong amplification of a single fragment of the expected molecular weight (based on homology to other reductases) were obtained using oligonucleotide combinations 424+426 (ca. 300 base pairs) and 425+427 (ca. 200 base pairs). Both reactions were scaled up 20-fold and included: 2×FailSafe buffer "F", 100 µL; 10×Cresol Red-sucrose loading dye, 20 µL; oligonucleotide (100 pmol/µL), 0.8 µL each; Z-Taq DNA polymerase, 1.0 µL; *P. putida* DNA (1 mg/mL), 1.0 µL; dH₂O, 73.4 µL. The entire reaction mix was electrophoresed on a 1.0% agarose gel for 2 hr at 100 v in TAE buffer (0.04 M Trizma base, 0.02 M acetic acid, and 0.001 M EDTA, pH 8.3) containing 0.5 µg/ml ethidium bromide. Fragments were excised from the gel and purified using the Qiagen Gel Purification Kit (Qiagen) before ligation to vector pCR2.1 (Invitrogen) according to the manufacturer's recommendations. Competent *Escherichia coli* DH10B cells (40 µL; Invitrogen) were transformed by electroporation using a BioRad GenePulser unit at 2.5 kV, 25 µF, and 200 Ω. SOC medium (960 µL; per liter, 5 g yeast extract, 20 g Bacto-tryptone, 580 mg NaCl, 186 mg KCl, 940 mg MgCl2, 1.2 g MgSO₄, and 3.6 g glucose) was added to the transformed cells and transferred to a 1.5 mL microfuge tube. The cells were shaken at 37° C. for 1 hr at 225 rpm and spread onto an LB agar plate containing 50 µg/mL kanamycin sulfate and 80 µg/mL of Bluo-gal (Invitrogen). The plates were incubated for 20 hr at 37° C. Colonies containing inserts were white amidst a background of blue colonies. Plasmid DNA was extracted from cultures of white kanamycin-resistant colonies obtained from both ligation/transformation reactions using the Qiagen Mini-Plasmid Purification Kit (Qiagen). In all instances, an insert of the expect size was obtained; samples of plasmid containing the ca. 300-bp fragment from ligation of the PCR reaction using oligos 424+426 was submitted for DNA sequencing. The sequence was homologous to the same proteins identified by the partial amino acids obtained from the purified SHBR. Therefore, oligos 424+426 were used to prepare a digoxygenin-labeled fragment using the PCR DIG Probe Synthesis Kit.

C. Southern Blot Hybridization

For Southern hybridization, *P. putida* genomic DNA was cleaved with a series of restriction endonucleases (ApaI, BamHI, BglII, EcoRI, EcoRV, HindIII, KpnI, SmaI, and XbaI). Reactions contained 5 µg DNA, appropriate buffer, and 20 units enzyme in 30 µL final volume. Digests were carried out for 3 hr at 37° C., then electrophoresed in a 0.8% TAE-agarose gel at 16 v for 18 hr. The DNA was transferred to Hybond N+ nylon filters under alkaline conditions using the VacuGene vacuum blotting unit. Hybridization of the labeled SHBR-specific PCR fragment to the blotted DNA digests was performed in EasyHyb solution (Roche) for 18 hr at 42° C. Stringency washes were carried out in 0.5×SSC (20×SSC=173.5 g NaCl and 88.2 g NaCl, pH 7.0), 0.1% sodium dodecyl sulfate at 68° C. for 2×15 minutes. Detection using a fluorescein-labeled, anti-digoxygenin antibody was performed as recommended by the manufacturer (Roche).

D. Cloning and Colony Hybridization:

Fifty µg of chromosomal DNA was cleaved with 100 U EcoRV in a total volume of 200 µL for 2 hr at 37° C. and electrophoresed as described above. The region from 4000-5000 base pairs was cut from the gel and the DNA purified. The isolated DNA was able to support amplification of a 300-base pair fragment by PCR using oligonucleotides 424+ 426. A sample of the isolated chromosomal DNA was ligated to pZerO2 vector DNA digested with SmaI, which is compatible with the blunt ends left by EcoRV at a 5:1 (insert:

vector) molar ratio in a total volume of 10 μl at 22° C. for 2 hr. DNA was precipitated by addition of 15 μl dH$_2$O and 250 μL 1-butanol, and pelleted at 12,000×g in a microcentrifuge for 5 min. Liquid was removed by aspiration, and the DNA was dried in a SpeedVac for 5 min under low heat. The pellet was resuspended in 5 μl dH$_2$O. The resuspended DNA was transformed by electroporation into 0.04 ml E. coli DH10B competent cells (Invitrogen) at 2.5 kV, 25 μF, and 200 □. SOC medium was immediately added (0.96 ml; SOC=0.5% yeast extract, 2% tryptone, 10 mM NaCl, 2.5 mM KCl, 10 mM MgCl$_2$, 10 mM MgSO$_4$, and 20 mM glucose per liter), and the cells incubated in a shaker for 1 hr at 37° C. and 225 rpm. Colonies containing recombinant plasmids were selected on LB agar plates containing 50 μg/ml kanamycin sulfate. Sufficient cells to give ca. 5,000 colonies were spread onto a 132 mm Hybond N+ membrane placed on top of LB agar medium containing 50 μg/ml kanamycin and incubated at 37° C. for 20 hr. Colonies were replicated onto two fresh filters that were placed on top of LB kanamycin agar medium. The filters were incubated at 37° C. for 4 hr. Colonies were lysed in situ by placing the filters on a piece of Whatman 3 MM paper saturated with 0.5 M NaOH for 5 min. The filters were dried for 5 min on Whatman paper, then neutralized on 3 MM paper soaked in 1.0 M Tris-HC1, pH 7.5 for 2 min, and dried for 2 min. Membranes were placed on top of 3 MM paper saturated with 1.0 M Tris-HC1, pH7.0/1.5 M NaCl for 10 min. DNA was crosslinked to the filters by exposure to ultraviolet light in a Stratagene UV Stratalinker 2400 set to "auto crosslink" mode. Cell debris was removed from the membranes by immersing in 3×SSC/0.1% SDS and wiping the surface with a wetted Kimwipe®, then incubating in the same solution heated to 65° C. for 3 hr with agitation. Filters were rinsed with dH$_2$O and used immediately or wrapped in SaranWrap® and stored at 4° C. Hybridization, washing, and detection of the colony blots were performed as described above using the labeled PCR probe. Positively hybridizing colonies were inoculated into LB-kanamycin liquid medium and grown at 37° C. for 24 hr, 250 rpm. Plasmid DNA was isolated using the Mini-Plasmid DNA kit from Qiagen and found to all possess an insert of ca. 4200 bp. To verify the SHBR gene was present in these isolates, PCR was performed as described in section 3. A using the plasmid DNA as template and the SHBR-specific primers 435 (5'-GCGGCTTGGC-CTGGGCTTGGTA-3', sense) and 436 (5'-CCCTTGC-GACGGCGTTGGTCATGA-3', anti-sense). The primers were derived from the sequence of the PCR fragment obtained using mixed oligonucleotides 424+426. One plasmid verified to contain the desired insert was chosen for further study and named "pSHBR4.2."

E. Determination and Analysis of the Nucleotide Sequence of pSHBR4.2

For rapid DNA sequencing of the insert in pSHBR4.2, primer sites were introduced at random using the New England Biolabs Genome Priming System kit. Colonies containing transposons in the plasmid were identified by selection on LB agar medium with kanamycin and chloramphenicol at 20 and 15 μg/mL, respectively. Colonies were grown, plasmid DNA extracted, and sequencing performed using the BigDye terminator kit and a model 377 DNA sequencing unit.

Nucleic acid and amino acid sequences for the gene are provided below as SEQ ID NO:5 and SEQ ID NO:6, respectively. The ketoreductase gene was identified as an open reading frame within the 4200-base pair insert on the basis of homology to previously identified amino acid sequences (underlined in the sequence given below):

```
Sequence of Ketoreductase gene cloned from
              Pseudomonas Putida

M A N S R T A L I I G A S R G
    1 ATGGCTAATTCAAGAACTGCCCTCATCATCGGCGCCTCGCGCGGG

L G L G L V Q R L H E D G W H
   46 CTTGGCCTGGGCTTGGTACAACGCCTGCACGAAGACGGCTGGCAC

I T A T V R N P Q Q P G D L A
   91 ATCACTGCCACCGTCCGTAACCCGCAGCAGCCCGGCGACCTGGCG

N V P G V R I E Q L E M N D T
  136 AACGTGCCCGGCGTGCGCATCGAGCAGTTGGAAATGAACGACACC

V Q L D D L K Q R L Q G Q V F
  181 GTCCAGCTCGATGACCTGAAGCAACGCCTGCAAGGCCAGGTGTTC

D L I F V N A G V M G P L P Q
  226 GACCTGATATTCGTCAACGCCGGGGTTATGGGCCCCCTGCCGCAA

D L E A V R N N D I G D L F M
  271 GACCTGGAGGCGGTACGCAACAACGACATTGGCGATCTGTTCATG

T N A V A P I R V A R R L V G
  316 ACTAACGCCGTGGCGCCGATACGCGTGGCTCGCCGCCTGGTGGGT

Q I R E G S G V L A F M S S I
  361 CAAATACGCGAAGGCAGCGGTGTGCTGGCCTTCATGAGCTCGATC

L G S V T I P D G G E I C L Y
  406 CTGGGAAGCGTCACCATACCCGACGGGGGCGAGATCTGCCTGTAC

K A S K A A L N S M I N S F F
  451 AAGGCCAGCAAGGCGGCACTGAACTCGATGATCAACAGCTTCTTC

V E Q Q R P D L C V L A M H P
  496 GTTGAGCAGCAGCGCCCGGACCTGTGCGTGCTGGCCATGCACCCG

G L G E N *
  541 GGGCTGGGTGAAAACTGA
```

This sequence encodes a protein of 186 amino acids with a molecular weight of 20.1 kD, in agreement with the size of the purified protein under denaturing conditions. Gel filtration chromatography indicated that the ketoreductase is a monomeric protein. A BLAST2 homology search revealed the most significant homology to short-chain dehydrogenases of Yersinia pestis (48% amino acid homology and 58% similarity as the amino acid level) and Pseudomonas aeruginosa (39% homology and 57% similarity).

A. Subcloning of the Ketoreductase Gene into E. coli Expression Vector pBMS2000

High-fidelity PCR amplification of the P. putida SHBR gene was carried out in two 100 μl aliquots, each containing Z-Taq reaction buffer, 0.2 mM each deoxynucleotide triphosphate (DATP, dCTP, dGTP, and dTTP), 0.4 nM each oligonucleotide, 2.5 U Z-Taq DNA polymerase (PanVera), and 10 pg plasmid DNA which contained the cloned P. putida SHBR gene. The amplification conditions included incubation at 94° C. for 4 min, followed by 25 cycles of incubation at 94° C. for 1 min; 50° C. for 1 min; and 72° C. for 1.5 min, using a Perkin-Elmer Model 480 thermocycler with autoextension. The PCR reaction mixture was extracted with an equal volume of 1:1 phenol:chloroform (GibcoBRL, Gaithersburg, Md.), and centrifuged at 12,000×g for 5 min. The upper aqueous phase was removed and placed in a new microcentrifuge tube. DNA was precipitated by addition of 0.1 vol 3 M sodium acetate and 2 vol ice-cold ethanol. After centrifugation at 12,000×g for 5 min, liquid was aspirated from the tube, and the pellet washed with 0.5 ml ice-cold 70% ethanol.

Liquid was aspirated again, and the pellet was allowed to air dry for 30 min at room temperature.

Amplified DNA was digested with 20 units each of NdeI and BamHI for 3 hr at 37° C. in a total volume of 50 µl. In parallel, the pBMS2000 vector (2 µg) was digested with NdeI and BamHI. The digested samples were electrophoresed on a 1.0% TAE agarose gel for 2 hr at 100 v. The bands corresponding to the SHBR gene (570-base pair fragment) and vector (4700-base pair fragment) were separately excised from the gel and purified using the QIAquick Gel Extraction Kit. The concentrations of the isolated fragments were estimated by electrophoresis against the low molecular weight mass ladder and ligated at a 5:1 (insert:vector) molar ratio in a total volume of 10 µl at 22° C. for 2 hr. DNA was precipitated by addition of 15 µL dH$_2$O and 250 µL 1-butanol, and pelleted at 12,000×g in a microcentrifuge for 5 min. Liquid was removed by aspiration, and the DNA was dried in a SpeedVac for 5 min under low heat. The pellet was resuspended in 5 µl dH$_2$O and transformed by electroporation into DH10B competent cells (Invitrogen) as previously described. Plasmids with the desired insert were identified by colony PCR. The reaction mixture (described above) was divided into 10-µl aliquots, and pipetted into the wells of a round-bottom microtiter plate. A kanamycin-resistant colony was picked using a disposable plastic inoculation needle, swirled into the reaction mixture, and transferred to LB-kanamycin agar. Thermocycling conditions using oligos 435 and 436 were as described in Section 3.A. Fifteen out of 29 colonies tested gave the expected PCR fragment. Restriction analysis of plasmid DNA from four of these colonies indicated they contained the cloned SHBR gene at the correct site of pBMS2000, and was named pBMS2000-SHBR.

B. Subcloning of the Ketoreductase Gene into *E. coli* Plasmid pBMS2000-PPFDH

The formate dehydrogenase gene from *Pichia pastoris* (PPFDH) was previously cloned and the corresponding protein overexpressed in *E. coli* as described in patent WO2003054155: The enzyme transfers reducing power (H$^+$) from formate to NAD$^+$ to provide co-factor recycling, thus eliminating the need for an exogenous enzyme such as glucose dehydrogenase. Formate can be added to reaction mixtures containing the PPFDH protein, or, preferably, formate is added to suspensions of recombinant *E. coli* cells expressing the protein.

pBMS2000-PPFDH (2 µg) was linearized with 10 U SmaI at 30° C. for 2 hr in a 50 µL reaction mix using buffer recommended by the manufacturer. Shrimp Alkaline Phosphatase (0.2 U) was then added and the sample incubated at 37° C. for 1 hr. The sample was brought to 0.1 mL with TE buffer and extracted with and equal volume of phenol:chloroform (1:1). The sample was centrifuged for 2 min and the upper phase retained. DNA was precipitated by addition of 0.1 vol 3 M sodium acetate (pH 7.5) and 2 vol 100% ethanol and pelleted by centrifugation for 12,000×g for 10 min. Liquid was removed by aspiration and the pellet washed once with 250 µL 70% ethanol. Ethanol was removed and the DNA dried in a SpeedVac for 5 min.

A PCR fragment containing the tac promoter and groES genes of pBMS2000 along with the ketoreductase gene was amplified from pBMS2000-RHBR using oligonucleotides 451 (5'-AGCTGTTTAAACTGCAACGTTACTC-CCCATCCCCCTGTTGAC-3'; sense) and 452 (5'-AGTCGTTTAAACGGATCCT-CAGTTTTCACCCAGCCCCGGGTG -3'; anti-sense) using previously described amplification conditions. The expected 1000-bp fragment (2.5 pg) was digested with 10 U PmeI in a total volume of 40 µL at 37° C. for 2 hr. The entire reaction mix was electrophoresed on a 1.0% TAE agarose gel for 1 hr at 100 v and the fragment purified using the QIAquick Gel Extraction Kit.

The tac-groES-SHBR fragment was ligated to SmaI-cut pBMS2000-PPFDH DNA in a 5:1 insert:vector molar ratio in a 10 µL volume with 1 U T4 DNA ligase (Invitrogen) at 16° C. for 4 hr. DNA was precipitated with 1-butanol and centrifuged at 12,000×g for 5 min. Supernatant was removed and the pellet dried in a SpeedVac for 5 min. DNA was resuspended in 5 µL dH$_2$O and 4 µL used to transform electrocompetent DH10B cells as previously described. Transformants were selected by plating onto LB-kanamycin agar and incubated in a 37° C. oven for 18 hr. Several colonies were tested for the presence of the SHBR gene using PCR as previously described. Analytical restriction endonuclease digests identified colonies containing plasmids with the PPFDH and SHBR genes and their associated promoter regions in parallel orientation. One such plasmid was retained for further work and named pBMS2000-PPFDH-SHBR.

C. Co-expression of the PPFDH and Ketoreductase Proteins in *E. coli* pBMS2000-PPFDH-ketoreductase was transformed into *E. coli* expression strains BL21, BL21(DE3)(CodonPlus RP), and JM110. For shake flask expression work, cells were initially grown in MT5 or MT5-M1+kanamycin medium for 20-24 hr, 30° C., 250 rpm. The composition of MT5 was given in Section 2.C. MT5-M1 is Hy-Pea, 2.0%; Tastone 154, 1.85%; Na$_2$HPO$_4$, 0.6%; (NH$_4$)$_2$SO$_4$ 0.125%; and glycerol, 4.0%. The medium is adjusted to pH to 7.2 with NaOH before autoclaving. After cooling, MgSO$_4$ is added to 0.0254% using a sterile 1 M solution.

The optical density at 600 nm (OD$_{600}$) of the cultures was recorded and fresh medium inoculated with the culture to a starting OD$_{600}$ of 0.30. The flask was incubated as described above until the OD$_{600}$ reached ~0.8-1.0. Isopropyl-thio-β-D-galactoside (IPTG) was added from a 1 M filter-sterilized stock in dH$_2$O to a final concentration of 35 µM or 1 mM and the culture allowed to grow for an additional 22 hr. Cells were harvested by centrifugation at 5,000×g at 4° C. in a Beckman JA 5.3 rotor. Medium was discarded and the pellet washed resuspended in an equal volume of 50 mM potassium phosphate buffer, pH 7.3. Cells were recentrifuged under identical conditions and the buffer removed. The wet cell weight was recorded and samples were stored frozen at −20° C. or used immediately for assays.

Relative expression levels of the recombinant enzyme were visualized by electrophoresis of samples of sonicated cell extracts on a sodium dodecyl sulfate-polyacrylamide gel (SDS-PAGE). To prepare extracts, the washed cell pellet was resuspended in 10 mM KPO$_4$ buffer, pH 7.3+1 mM dithiothreitol (DTT) at 10 mL/g wet cell weight. An 0.8 mL sample was dispensed into a chilled 1.5 mL microfuge tube and sonicated for 3×15 sec at power setting "15" with a Fisher Sonic Dismembrator). Debris was removed by centrifugation at 12,000×g for 5 min. The supernatant, which contained soluble protein, was retained. One µL of the extract was mixed with 5 µL 4×NuPAGE loading buffer (Invitrogen) and 13 µL dH$_2$O and heated at 70° C. for 10 min. One µL of 1 M DTT was then added and 5 µL of the sample applied to a 12% NuPAGE Bis-Tris polyacrylamide mini-gel (Invitrogen). Samples were electrophoresed for 1 hr at 200 v with NuPAGE MOPS-SDS buffer (Invitrogen). Proteins were stained using a 0.1% Coomassie Blue solution in a 50:40:10 dH$_2$O:methanol:acetic acid and destained in the same solution without dye. Two proteins of ~20 kDa ketoreductase and 40 kDa (PPFDH) were present in all recombinant strains.

EXAMPLE 9

Purification of Ketoreductase from *Hansenula* Polymorph Cloning of Ketoreductase in *Escherichia coli* to Produce *Escherichia coli* JM110(pBMS2000-SCGD-RHBR)

*Hansenula polymorha* cells were suspended at 10% (w/v, wet cells) in 500 mL of buffer A (10 mM phosphate buffer, pH 6.1 containing 10% glycerol, 1 mM DTT, 1 mM EDTA). The cell suspension was passed twice through a microfluidzer at 12,000 psi. The disintegrated cells were centrifuged at 25,000×for 15 min at 4° C. to obtain cell extracts. The cell extract was loaded on to a 10-mL column (two Pharmacia 5-mL bluegel affinity columns connected in a row) at a flow rate of 1 mL/min. The column was washed with 40 mL of buffer A. The column was eluted with buffer A containing a gradient of NADP increasing from 0 mM to 10 mM. The reductase activity was eluted in fractions containing 0.25-0.5 mM NADP. Fractions containing activity were pooled and concentrated with an Amicon 10K Centriprep to 1 mL. The concentrated enzyme fraction was loaded onto a 84×2.5 cm Sephacryl S-200 column. Fractions of 8 mL were collected. Fractions containing enzyme activity (fractions 33-35) were pooled and concentrated by an Amicon 10K Centricon to 600 ☐L. The concentrated fraction was loaded onto a S75 Sephadex (FPLC) column and 1-mL fractions were collected. The enzyme activity was present in fractions 13 and 14. Both fractions were analyzed by 12.5% SDS-PAGE demonstrated a single protein band.

The NADP-dependent dehydrogenase was purified to homogeneity from cell extracts of *Hansenula polymorpha*. The sub-unit molecular weight of the enzyme is 35,000 daltons based on SDS/PAGE. The purified protein was blotted on to a PVDF-membrane according to the manufactures instructions (Bio-Rad). The purified protein was stained with coomassie blue and the protein band was excised from the membrane. The excised protein was then sent out for sequencing to Argo Bioanalytica. The peptide sequences obtained from Argo Bioanalytica are as follows:

Peptide 1: LNTGASIPSVALGCWQSSPEDTYTSVLAALK

Peptide 2: GIVVEAYSPLGSAGS

Peptide 3: HIDTAHVYR

Peptide 4: ILNPDWGVPVYNDEEDNF

A strong homology was found to glycerol dehydrogenase, aldehyde reductase and various other NADP-dependent dehydrogenases with the above peptide sequences. These peptide sequences were used to prepare probes for cloning and expression of the enzyme.

A. Preparation of RHBR Ketoreductase-specific Probe

*Hansenula polymorpha* ATCC 66057 (recently reclassified as *Pichia angusta*) was grown in YPD medium (1.0% Bacto yeast extract, 2.0% Bacto peptone, 2.0% dextrose) at 30° C. with vigorous shaking. After 24 hr, cells were harvested by centrifugation and immediately used or stored as a pellet at –20° C. until needed. The cells were harvested by centrifugation and chromosomal DNA was prepared using the procedure described in Ausubel et al. (eds.) Current Protocols in Molecular Biology, vol. 2, section 13.11.2 (1991), John Wiley and Sons, New York.

A sample of the purified ketoreductase protein was submitted for partial amino acid sequencing following tryptic digestion. Four sequences were obtained: LNTGASIPSVAL-GCWQSSPEDTYTSVLAALK (N-terminus), GIVVEAYSPLGSAGS, HIDTAHVYR, and ILNPD-WGVPVYNDEEDNF (putative COOH-terminus). A BLAST2 homology search using the above sequences showed significant regions of homology to other reductases and dehydrogenases such as those reacting with aldose, aldehyde, uronate, and glycerol. For use in polymerase chain reaction (PCR), degenerate oligonucleotide primers were prepared based on the corresponding codons of the amino acids according to Table 6. The direction of the primers (i.e., sense and/or anti-sense) were determined using the likely location of the amino acid sequence within the protein by comparison to homologous dehydrogenases/reductases.

TABLE 6

| Primer name | Nucleotide sequence | Corresponds to (direction) |
|---|---|---|
| Oligo 353 | GTIGCIYTIGGITGYTGGCAR | VALGCWQ (sense) |
| Oligo 354 | CCIGARGAYACITAYCAIWS | PEDTYTS (sense) |
| Oligo 355 | RTAIGCYTCIACIACIATICC | GIVVEAY (anti-sense) |
| Oligo 361 | CAYATIGAYACIGCICAYGTITA | HIDTAHVY (sense) |
| Oligo 362 | AARTTRTCYTCYTCRTCRTTRTA | YNDEEDNF (anti-sense) |
| Oligo 363 | GGIATIGTIGTIGARGCITA | GIVVEAY (sense) |

Standard nucleoside bases (adenosine, thymine, cytosine, and guanosine) are indicated by "A", "T", "C", or "G". "I"=inosine (replaces all four bases). Mixed bases are: "R" (A+G); "S" (C+G); "W" (A+T); "Y" (C+T). Amino acid abbreviations correspond to those designated by the International Union of Pure and Applied Chemistry (IUPAC). Combinations of sense and anti-sense primers were tried with the FailSafe series of PCR buffer and *H. polymorpha* chromosomal DNA as template in 10 μL reactions. Amplification was carried out in a Hybaid PCR Express thermocycler using a five-stage "touchdown" PCR strategy:

| Stage 1 | Stage 2 | Stage 3 | Stage 4 | Stage 5 |
|---|---|---|---|---|
| 94° 1 min | 94° 30 sec | 94° 30 sec | 94° 30 sec | 72° 5 min |
|  | 55° 30 sec | 55°-->40° 30 sec | 40° 30 sec |  |
|  | 72° 30 sec | 72° 30 sec | 72° 30 sec |  |
| 1 cycle | 4 cycles | 20 cycles | 5 cycles |  |

Strong amplification of a single fragment of the expected molecular weight (based on homology to other reductases) were obtained using oligonucleotide combinations 361+362 (ca. 750 base pairs) and 362+363 (ca. 300 base pairs). The former reaction was scaled up 20-fold and included: 2×Fail-Safe buffer "B", 100 μL; 10×Cresol Red-sucrose loading dye, 20 μL; oligonucleotide (100 pmol/μL), 0.8 μL each; Z-Taq DNA polymerase, 1.0 μL; *H. polymorpha* DNA (1 mg/mL), 1.0 μL; dH$_2$O, 73.4 μL. The entire reaction mix was electrophoresed on a 1.0% agarose gel for 2 hr at 100 v in TAE buffer (0.04 M Trizma base, 0.02 M acetic acid, and 0.001 M EDTA, pH 8.3) containing 0.5 μg/ml ethidium bromide. The fragment was excised from the gel and purified using the Qiagen Gel Purification Kit (Qiagen) before ligation to vector pTOPO-TA (Invitrogen) according to the manufacturer's recommendations. Competent *Escherichia coli* DH10B cells (40 μL; Invitrogen) were transformed by electroporation using a BioRad GenePulser unit at 2.5 kV, 25 μF, and 200 ☐ SOC medium (960 μL; per liter, 5 g yeast extract, 20 g Bactotryptone, 580 mg NaCl, 186 mg KCl, 940 mg MgCl2, 1.2 g MgSO4, and 3.6 g glucose) was added to the transformed cells and transferred to a 1.5 mL microfuge tube. The cells were shaken at 37° C. for 1 hr at 225 rpm and spread onto an LB agar plate containing 50 μg/mL kanamycin sulfate. The plate was incubated for 20 hr at 37° C. Plasmid DNA was extracted from cultures of kanamycin-resistant colonies using the Qiagen Mini-Plasmid Purification Kit (Qiagen) and submitted for sequencing of the PCR fragment. For further analytical work, two primers (oligos 368 and 369; 5'-CAGAT-GCCGAGGAACAGTGGTTCC-3' and 5'-CGAGAGCAAT-GATGTCCTCGTCCT-3', respectively) were prepared based on the DNA sequence obtained. These primer permit amplification of a 348-base pair region in the putative center of the RHBR gene. They were used to prepare a digoxygenin-labeled fragment using the PCR DIG Probe Synthesis Kit.

B. Southern Blot Hybridization

For Southern hybridization, *H. polymorpha* genomic DNA was cleaved with a series of restriction endonucleases (BglII, ClaI, EcoRV, and HindIII). Reactions contained 5 μg DNA, appropriate buffer, and 20 units enzyme in 30 μL final volume. Digests were carried out for 3 hr at 37° C., then electrophoresed in a 0.8% TAE-agarose gel at 16 v for 18 hr. The DNA was transferred to Hybond N+ nylon filters under alkaline conditions using the VacuGene vacuum blotting unit. Hybridization of the labeled RHBR-specific PCR fragment to the blotted DNA digests was performed in EasyHyb solution (Roche) for 18 hr at 42° C. Stringency washes were carried out in 0.5×SSC (20×SSC=173.5 g NaCl and 88.2 g NaCl, pH 7.0), 0.1% sodium dodecyl sulfate at 68° C. for 2×15 minutes. Detection using a fluorescein-labeled, anti-digoxygenin antibody was performed as recommended by the manufacturer (Roche).

C. Cloning and Colony Hybridization

Ten μg of chromosomal DNA was cleaved with 25 U BglII in a total volume of 50 μL for 3 hr at 37° C. and electrophoresed as described above. The region from 6500-7500 base pairs was cut from the gel and the DNA purified. The isolated DNA was able to support amplification of a 750-base pair fragment by PCR using oligonucleotides 361+362. A sample of the isolated chromosomal DNA was ligated to pZerO2 vector DNA digested with BamHI (the overhanging 5' nucleotides are compatible with those of BglII) at a 5:1 (insert: vector) molar ratio in a total volume of 10 μl at 22° C. for 2 hr. DNA was precipitated by addition of 15 μl dH$_2$O and 250 μL 1-butanol, and pelleted at 12,000×g in a microcentrifuge for 5 min. Liquid was removed by aspiration, and the DNA was dried in a SpeedVac for 5 min under low heat. The pellet was resuspended in 5 μl dH$_2$O. The resuspended DNA was transformed by electroporation into 0.04 ml *E. coli* DH10B competent cells (Invitrogen) at 25 μF and 250 ☐. SOC medium was immediately added (0.96 ml; SOC=0.5% yeast extract, 2% tryptone, 10 mM NaCl, 2.5 mM KCl, 10 mM MgCl$_2$, 10 mM MgSO$_4$, and 20 mM glucose per liter), and the cells incubated in a shaker for 1 hr at 37° C. and 225 rpm. Colonies containing recombinant plasmids were selected on LB agar plates containing 50 μg/ml kanamycin sulfate Sufficient cells to give ca. 15,000 colonies were spread onto a 132 mm Hybond N+ membrane (Amersham Pharmacia) placed on top of LB agar medium containing 50 μg/ml kanamycin and incubated at 37° C. for 20 hr. Colonies were replicated onto two fresh filters that were placed on top of LB kanamycin agar medium. The filters were incubated at 37° C. for 4 hr. Colonies were lysed in situ by placing the filters on a piece of Whatman 3 MM paper saturated with 0.5 M NaOH for 5 min. The filters were dried for 5 min on Whatman paper, then neutralized on 3 MM paper soaked in 1.0 M Tris-HCl, pH 7.5 for 2 min, and dried for 2 min. Membranes were placed on top of 3 MM paper saturated with 1.0 M Tris-HCl, pH7.0/1.5 M NaCl for 10 min. DNA was crosslinked to the filters by exposure to ultraviolet light in a Stratagene UV Stratalinker 2400 set to "auto crosslink" mode. Cell debris was removed from the membranes by immersing in 3×SSC/0.1% SDS and wiping the surface with a wetted Kimwipe®, then incubating in the same solution heated to 65° C. for 3 hr with agitation. Filters were rinsed with dH$_2$O and used immediately or wrapped in SaranWrap® and stored at 4° C. Hybridization, washing, and detection of the colony blots were performed as described above using the labeled PCR probe. Positively hybridizing colonies were inoculated into LB-kanamycin liquid medium and grown at 37° C. for 24 hr, 250 rpm. Plasmid DNA was isolated using the Mini-Plasmid DNA kit from Qiagen. To verify the RHBR gene was present in these isolates, PCR was performed using the plasmid DNA as template and the RHBR-specific primers 368+369. One plasmid verified to contain the desired insert was chosen for further study and named "pRHBR7.0."

D. Determination and Analysis of the Nucleotide Sequence of Ketoreductase pRHBR7.0

For rapid DNA sequencing of the insert in pRHBR7.0, primer sites were introduced at random using the New England Biolabs Genome Priming System kit. Colonies containing transposons in the plasmid were identified by selection on LB agar medium with kanamycin and chloramphenicol at 20 and 15 μg/mL, respectively. The plate was sent to the Bristol-Myers Squibb Core Sequencing Facility, where the colonies were grown, plasmid DNA extracted, and sequencing performed using the BigDye terminator kit and a model 377 DNA sequencing unit.

The nucleic acid sequence (SEQ ID NO:7) and the amino acid sequence (SEQ ID NO: 8) of the RHBR ketoreductase gene is shown below. The gene was identified as an open reading frame within the 7000-base pair insert on the basis of homology to previously identified amino acid sequences (underlined in the sequence given below):

```
Nucleotide Sequence of ketoreductase pRHBR7.0

M A S I C T K T Q K L N T G A
  1 ATGGCTTCTATTTGCACAAAGACTCAAAAGCTCAACACTGGCGCC

S I P S V A L G C W Q S S P E
 46 TCAATCCCTTCAGTTGCCCTGGGATGCTGGCAATCGTCCCCCGAG

D T Y T S V L A A L K A G Y R
 91 GACACCTACACTTCTGTTTTGGCCGCATTGAAGGCAGGCTACAGA

H I D T A H V Y R N E A D V G
136 CATATCGACACCGCGCACGTGTACCGGAACGAGGCGGATGTTGGT

R A I K D S G V P R E S L F I
181 AGAGCCATCAAAGACTCGGGGGTTCCTAGAGAGTCGCTCTTCATC

T T K L W N T N H R D P L A A
226 ACTACGAAGCTCTGGAACACCAACCACAGAGACCCATTGGCTGCT

L N G S L E R L G M D Y V D L
271 CTGAATGGCTCGTTGGAGAGACTCGGCATGGATTACGTCGATCTG
```

-continued

| Nucleotide Sequence of ketoreductase pRHBR7.0 |
|---|
|     Y  L  V  H  W  P  V  P  F  V  K  P  S  P  D<br>316 TATCTGGTGCACTGGCCTGTTCCTTTTGTTAAGCCTTCGCCAGAT |
|     A  E  E  Q  W  F  P  K  D  P  N  N  P  E  K<br>361 GCCGAGGAACAGTGGTTCCCAAAGGATCCTAACAATCCGGAAAAG |
|     F  H  N  D  K  D  W  D  F  I  K  T  W  E  L<br>406 TTCCACAATGACAAAGATTGGGACTTCATCAAGACGTGGGAACTG |
|     V  Q  Q  L  P  K  D  K  A  R  A  V  G  V  S<br>451 GTCCAACAGCTGCCTAAGGACAAGGCCCGGGCCGTGGGCGTGTCT |
|     N  M  S  K  T  N  L  E  K  L  L  A  A  P  T<br>496 AACATGTCCAAGACAAACTTGGAGAAGCTGCTAGCTGCGCCAACG |
|     T  K  V  V  P  A  A  N  Q  V  E  M  H  P  F<br>541 ACCAAGGTCGTTCCTGCAGCCAACCAGGTCGAAATGCACCCATTC |
|     Y  P  R  H  Q  L  L  E  Y  C  K  E  K  G  I<br>586 TACCCGCGCCACCAGCTGCTCGAGTACTGCAAGGAGAAAGGCATT |
|     V  V  E  A  Y  S  P  L  G  S  A  G  S  P  L<br>631 GTTGTGGAGGCGTACTCGCCACTGGGCAGTGCTGGGTCGCCACTA |
|     L  K  D  E  D  I  I  A  L  A  D  K  K  G  I<br>676 CTTAAGGACGAGGACATCATTGCTCTCGCCGACAAGAAGGGCATT |
|     S  P  A  C  L  L  I  S  W  A  L  H  R  D  T<br>721 TCTCCAGCCTGTCTGCTGATTTCGTGGGCTCTTCACAGAGACACT |
|     V  V  L  P  K  S  V  T  P  S  R  I  E  A  N<br>766 GTCGTGCTGCCAAAGAGCGTGACTCCGTCGCGGATCGAGGCCAAC |
|     I  K  V  V  D  L  D  D  E  T  A  D  A  L  S<br>811 ATCAAGGTCGTCGACCTCGACGACGAGACCGCTGACGCCCTGTCG |
|     A  L  Y  K  T  K  G  R  R  I  L  N  P  D  W<br>856 GCGCTCTACAAGACCAAGGGTAGAAGAATTCTGAACCCTGACTGG |
|     G  V  P  V  Y  N  D  E  E  D  N  F  *<br>901 GGTGTTCCAGTCTACAACGACGAAGAAGACAACTTTTAG |

E. Analysis of the RHBR Gene

No introns were present in this gene. This sequence encodes a protein of 312 amino acids with a molecular weight of 34.8 kD, in agreement with the size of the purified protein under denaturing conditions. Gel filtration chromatography indicated that the RHBR ketoreductase is a monomeric protein. A BLAST2 homology search revealed significant homology to β-keto ester reductases of *Saccharomyces cerevisiae* involved in arabanose and uronate biosynthesis (55% amino acid homology and 69% similarity as the amino acid level). These enzymes are members of the short-chain reductases/dehydrogenasaes F. Subcloning of the RHBR Gene into *E. coli* Expression Vector pBMS2000

Oligonucleotide primers were prepared containing 1) an NdeI site followed by the first 24 nucleotides of the RHBR gene (5'-GATCCATATGGCTTCTATTTGCACAAAGAC T-3') and 2) the last 24 nucleotides of the RHB gene (including stop codon) followed by a SmaI restriction site (anti-sense of the complementary strand; 5'-GAT CCCCGGGCTAAAAGTTGTCTTCCTCGTC-3'). High-fidelity PCR amplification of the *H. polymorpha* RHBR ketoreductase gene was carried out in two 100 μl aliquots, each containing Z-Taq reaction buffer, 0.2 mM each deoxynucleotide triphosphate (dATP, dCTP, dGTP, and dTTP), 0.4 nM each oligonucleotide, 2.5 U Z-Taq DNA polymerase (PanVera), and 10 pg plasmid DNA which contained the cloned *H. polymorpha* RHBR ketoreductase gene. The amplification conditions included incubation at 94° C. for 4 min, followed by 25 cycles of incubation at 94° C. for 1 min; 50° C. for 1 min; and 72° C. for 1.5 min, using a Perkin-Elmer Model 480 thermocycler with autoextension. The PCR reaction mixture was extracted with an equal volume of 1:1 phenol:chloroform, and centrifuged at 12,000×g for 5 min. The upper aqueous phase was removed and placed in a new microcentrifuge tube. DNA was precipitated by addition of 0.1 vol 3 M sodium acetate and 2 vol ice-cold ethanol. After centrifugation at 12,000×g for 5 min, liquid was aspirated from the tube, and the pellet washed with 0.5 ml ice-cold 70% ethanol. Liquid was aspirated again, and the pellet was allowed to air dry for 30 min at room temperature.

At this time DNA sequence analysis revealed that the RHBR ketoreductase gene contained an internal SmaI restriction site, so this enzyme could not be used for digestion of the PCR product. As an alternative, the 3' end of the PCR product was used without treatment with SmaI. Due to the nature of the DNA polymerase used, it should contain a mixture of "A" overhangs and blunt-ended fragments; the latter type of fragment should ligate to the blunt end left by SmaI upon cleavage of pBMS2000. Amplified DNA was digested with 20 units of NdeI for 3 hr at 37° C. in a total volume of 50 μl. In parallel, the pBMS2000 vector (2 pg) was digested with NdeI and SmaI. The digested samples were electrophoresed on a 1.0% TAE agarose gel for 2 hr at 100 v. The bands corresponding to the RHBR ketoreductase gene (950-base pair fragment) and vector (4700-base pair fragment) were separately excised from the gel and purified using the QIAquick Gel Extraction Kit. The concentrations of the isolated fragments were estimated by electrophoresis against the low molecular weight mass ladder and ligated at a 5:1 (insert:vector) molar ratio in a total volume of 10 μl at 22° C. for 2 hr. DNA was precipitated by addition of 15 μL dH$_2$O and 250 μL 1-butanol, and pelleted at 12,000×g in a microcentrifuge for 5 min. Liquid was removed by aspiration, and the DNA was dried in a SpeedVac for 5 min under low heat. The pellet was resuspended in 5 μl dH$_2$O and transformed by electroporation into DH10B competent cells (Invitrogen) as previously described. Plasmids with the desired insert were identified by colony PCR. The reaction mixture (described above) was divided into 10-μl aliquots, and pipetted into the wells of a round-bottom microtiter plate. A kanamycin-resistant colony was picked using a disposable plastic inoculation needle, swirled into the reaction mixture, and transferred to LB-kanamycin agar. Thermocycling conditions were as described in Section 1A. Nine out of 18 colonies tested gave the expected PCR fragment of 950 bp. Restriction analysis of plasmid DNA from four of these colonies indicated they contained the cloned RHBR gene at the correct site of pBMS2000, and was named pBMS2000-RHBR.

G. Subcloning of the RHBR Gene into *E. coli* Plasmid pBMS2000-SCGD

The glucose-6-phosphate dehydrogenase gene from *Saccharomyces cerevisiae* (SCGD) was previously cloned and the corresponding protein overexpressed in *E. coli*. The enzyme transfers reducing power (H$^+$) from glucose-6-phosphate (G-6-P) to NADP$^+$ to provide co-factor recycling, thus eliminating the need for an exogenous enzyme such as glucose dehydrogenase. G-6-P can be added to reaction mixtures containing the SCGD protein, or, preferably, glucose is added to suspensions of recombinant *E. coli* expressing the protein; as part of the active transport mechanism, the glucose is phosphorylated to G-6-P by the bacterial cell.

pBMS2000-SCGD (2 μg) was linearized with 10 U SmaI at 30° C. for 2 hr in a 50 μL reaction mix using buffer recommended by the manufacturer (Invitrogen). Shrimp Alkaline Phosphatase (0.2 U) was then added and the sample incubated at 37° C. for 1 hr. The sample was brought to 0.1 mL with TE buffer and extracted with and equal volume of phenol:chloroform (1:1;). The sample was centrifuged for 2 min and the upper phase retained. DNA was precipitated by addition of 0.1 vol 3 M sodium acetate (pH 7.5) and 2 vol 100% ethanol and pelleted by centrifugation for 12,000×g for 10 min. Liquid was removed by aspiration and the pellet washed once with 250 μL 70% ethanol. Ethanol was removed and the DNA dried in a SpeedVac for 5 min.

A PCR fragment containing the tac promoter and groES genes of pBMS2000 along with the RHBR gene was amplified from pBMS2000-RHBR using oligonucleotides 299 (AGCTCCCGGGTGCAACGTTACTC-CCCATCCCCCTGTTGAC) and 371 (GATC-CCCGGGCTAAAAGTTGTCTTCCTCGTC) using previously described amplification conditions. The expected 1550-bp fragment was ligated to pCR2.1 (Invitrogen). Transformants were screened for the presence of an insert by colony PCR. Plasmid DNA from positive colonies (ca. 2 μg) was prepared and digested with restriction endonucleases KpnI+EcoRV using 10 U of each enzyme in a 40 μL reaction volume with Invitrogen buffer "3" for 2 hr at 37° C. Five units of T4 DNA polymerase (Invitrogen) was added to the reaction and the sample incubated at 11° C. for 20 min to remove single-stranded DNA overhangs. The entire reaction mix was electrophoresed on a 1.0% TAE agarose gel for 1 hr at 100 v and the fragment purified using the QIAquick Gel Extraction Kit.

The tac-groES-RHBR fragment was ligated to SmaI-cut pBMS2000-SCGD DNA in a 5:1 insert:vector molar ratio in a 10 μL volume with 1 U T4 DNA ligase (Invitrogen) at 16° C. for 4 hr. DNA was precipitated with 1-butanol and centrifuged at 12,000×g for 5 min. Supernatant was removed and the pellet dried in a SpeedVac for 5 min. DNA was resuspended in 5 μL dH$_2$O and 4 μL used to transform electrocompetent DH10B cells as previously described. Transformants were selected by plating onto LB-kanamycin agar and incubated in a 37° C. oven for 18 hr. To determine the presence and orientation of the insert, two new primers (oligo 395; GTGACTAAGCCAGAAGATACGAAG and oligo 369; CGAGAGCAATGATGTCCTCGTCCT) that was homologous to the sense strand at the 3' end of bp 1487-1511 of the SCGD gene and to the anti-sense strand of bp 673-649 of the RHBR gene, respectively, were prepared. A PCR reaction using these primers as previously described was performed. If the SCGD and RHBR genes are present in parallel orientation, a fragment of ca. 1300 bp should be amplified. Two out of 16 kanamycin-resistant colonies tested supported the expected amplification. Digestion with a series of diagnostic restriction endonucleases confirmed the structure of the plasmid, named pBMS2000-SCGD-RHBR.

H. Expression of the RHBR Ketoreductase Protein in *E. coli* pBMS2000-RHBR was transformed into *E. coli* expression strains BL21, JM110, and W3110. For shake flask expression work, cells were initially grown in MT5+kanamycin for 20-24 hr, 30° C., 250 rpm. MT5 is 2.0% Yeastamin, 4.0% glycerol, 0.6% Na$_2$HPO$_4$, 0.3% KH$_2$PO$_4$, 0.125% (NH$_4$)$_2$SO$_4$, and 0.0256% MgSO$_4$.7H$_2$O. The optical density at 600 nm (OD$_{600}$) was recorded and fresh medium inoculated with the culture to a starting OD$_{600}$ of 0.30. The flask was incubated as described above until the OD$_{600}$ reached ~0.8-1.0. Isopropyl-thio-β-D-galactoside (IPTG) was added from a 1 M filter-sterilized stock in dH$_2$O to a final concentration of 50 μM or 1 mM and the culture allowed to grow for an additional 24 or 48 hr. Cells were harvested by centrifugation at 5,000×g at 4° C. in a Beckman JA 5.3 rotor. Medium was discarded and the pellet washed resuspended in an equal volume of 50 mM potassium phosphate buffer, pH 7.3. Cells were recentrifuged under identical conditions and the buffer removed. The wet cell weight was recorded and samples were stored frozen at −20° C. or used immediately for assays. Subsequently, experiments using MT5-Hy Rice and MT5-Hy Pea were conducted using the strain demonstrating the best enzyme activity. MT5-Hy Rice and MT5-Hy Pea contained 2.0% of the indicated medium supplement in place of yeastamin.

C. Co-expression of SCGD and RHBR Ketoreductase in *E. coli* pBMS2000-SCGD-RHBR was transformed into *E. coli* strains BL21(DE3)Star and JM110 by electroporation. A single colony of each tranformant was used to inoculate 20 mL MT5-Hy Pea medium+50 μg/mL kanamycin in a 50 mL flask. Growth, induction, and harvesting of cell cultures were performed as described in the previous section. Use of the recombinant RHBR ketoreductase enzyme catalyzed the conversion of compound 2 to compound 3 described herein.

The contents of all patents, patent applications, published articles, books, reference manuals, texts and abstracts cited herein are hereby incorporated by reference in their entirety to more fully describe the state of the art to which the invention pertains. The foregoing description and examples are not intended in any respect to limit the scope of the potential embodiments of the claimed invention.

What is claimed is:

1. A process for the preparation of a compound of Formula Ib

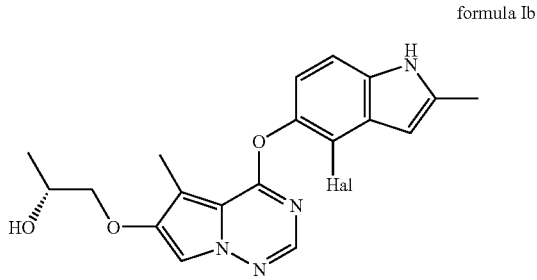

formula Ib wherein Hal is a halogen,
comprising reducing a ketone compound of Formula IIb

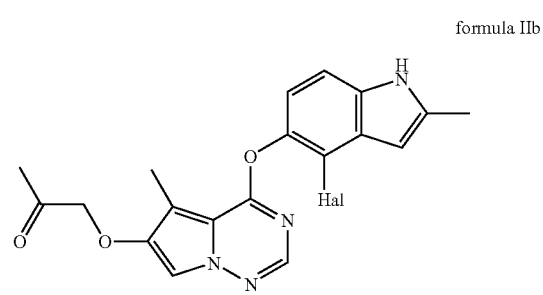

formula IIb by contacting with the oxidoreductase enzyme produced by *Pichia* having SEQ ID NO: 2 and thereby producing the compound of formula Ib.

2. The process of claim 1 wherein the reaction with the oxidoreductase enzyme is carried out either by:
    (a) introducing a ketone compound of formula IIb into a medium in which the microorganism is being fermented to form a reaction mixture in which the oxidoreductase enzyme is concurrently being formed and contacted with the ketone compound; or
    (b) fermenting the microorganism until sufficient growth is realized, then introducing the ketone compound to form a reaction mixture in which the ketone compound of formula IIb is contacted with the oxidoreductase enzyme.

3. The process of claim 1 wherein the amount of the ketone compound of formula IIb added to the reaction mixture is up to about 100 g/L of the reaction mixture.

4. The process of claim 1 further comprising isolating, and optionally purifying, the compound of formula Ib.

5. The process of claim 1 wherein the reaction with the oxidoreductase enzyme is carried out by contacted the ketone compound of formula IIb with the oxidoreductase enzyme that was previously isolated and optionally purified before contacting with the ketone compound.

6. The process of claim 5 wherein the oxidoreductase enzyme is derived from cell extracts.

7. The process of claim 1 wherein the oxidoreductase enzyme is provided from a microorganism selected from the group consisting of *Pichia angusta*, and *Pichia methanolica*.

8. The process of claim 1 wherein the oxidoreductase enzyme is provided by introducing a plasmid controlling its expression into *E. coli* host cells.

9. The process of claim 1 wherein the oxidoreductase enzyme is expressed by a gene having sequence SEQ ID NO:1.

10. The process of claim 2, step (a), wherein the oxidoreductase enzyme provides a reaction yield of greater than 70% by weight of the compound of formula Ib, based on the total weight of the reaction mixture.

11. The process of claim 10 wherein the oxidoreductase provides the compound of formula Ib in an enantiomeric purity greater than 93%.

12. The process of claim 1 wherein the reaction with the oxidoreductase enzyme is carried out at a pH of between about 4.0 and about 9.0.

13. The process of claim 1 wherein the compound of formula Ib is and the compound of formula IIb is
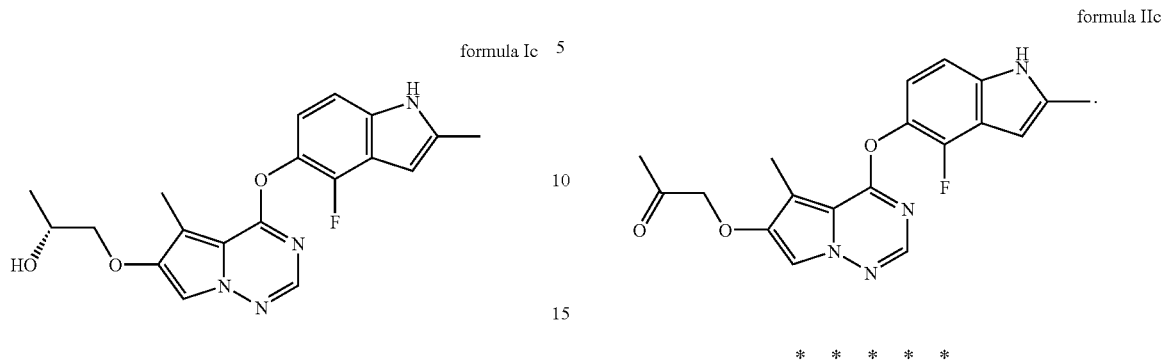
* * * * *

UNITED STATES PATENT AND TRADEMARK OFFICE
CERTIFICATE OF CORRECTION

PATENT NO. : 7,393,667 B2  
APPLICATION NO. : 11/421112  
DATED : July 1, 2008  
INVENTOR(S) : Patel et al.

Page 1 of 1

It is certified that error appears in the above-identified patent and that said Letters Patent is hereby corrected as shown below:

<u>On the Title Page,</u>

Item (75) Inventors should read:

-- Ramesh N. Patel, Bridgewater, NJ (US); Linda Nga Hoong Chu, East Brunswick, NJ (US); Robert M. Johnston, Whitehouse Station, NJ (US); Zhiwei Guo, Franklin Park, NJ (US); Yijun Chen, Belle Mead, NJ (US); Steven L. Goldberg, Basking Ridge, NJ (US); Ronald L. Hanson, Morris Plains, NJ (US); Animesh Goswami, Plainsboro, NJ (US); Kishta Katipally, Monmouth Junction, NJ (US) --

Signed and Sealed this

Sixth Day of January, 2009

JON W. DUDAS  
*Director of the United States Patent and Trademark Office*

SEQUENCE LISTING

```
<160> NUMBER OF SEQ ID NOS: 8

<210> SEQ ID NO 1
<211> LENGTH: 822
<212> TYPE: DNA
<213> ORGANISM: Pichia angusta

<400> SEQUENCE: 1
atgaacatta  tcggaaatta  cgacaagcta  ccaaccgagg  ctcctcaatt  gccttccaac      60
gttttcagcc  tgttctccct  gaaaggcaag  gtggccagca  ttactggtgg  ctcgacagga     120
attggtctgg  ctgtggcaga  agcgtatgct  caggcaggcg  cagacgtggc  catctggtac     180
```

```
aacagcacaa acgctgacca cgaagctgag aggctgtcca agacgtacgg gatccgtgcc    240
aaggcttaca agtgcgcagt gggcgacttt gaccaggtca aggccacgat cgatgccatt    300
gagtctgact ttggcacgat tcacattttt gttgcaaatg cggggattgg ctcccaatcg    360
gtgcctgtga tcgatgcgtc gctggaaaaa taccgggcaa tcatgaacac gaatttggac    420
ggcgtgtact actgcgccaa gtgcgtgggt ccaattttca gaagcacgg caagggttcc     480 tttatcatca ccacctcaca ggcagcccat attgtcacgg ctcacgtgtg caagcggct     540 tacaacgcca gcaaggcagc gtgcatccag attgccaaga gtctggcaat ggaatgggtc    600
ggcttcgccc gtgtcaatac gatctctcca gggtacattg tcaccccta ctcgaaagat     660 gtgcctaacg aggagaaagt caagtggtgc acgttgatcc caatgggcag agagggcttg    720
cctcaagagc ttgtgggcgc atacctgtac tttgcgtcgg acgcctcaac cttcaccacc    780
ggcgctgacc tcatcattga cggtggttat tgctgcccat aa                      822
```

<210> SEQ ID NO 2
<211> LENGTH: 273
<212> TYPE: PRT
<213> ORGANISM: Pichia angusta
<400> SEQUENCE: 2

```
Met Asn Ile Ile Gly Asn Tyr Asp Lys Leu Pro Thr Glu Ala Pro Gln
1               5                   10                  15

Leu Pro Ser Asn Val Phe Ser Leu Phe Ser Leu Lys Gly Lys Val Ala
            20                  25                  30

Ser Ile Thr Gly Gly Ser Thr Gly Ile Gly Leu Ala Val Ala Glu Ala
        35                  40                  45

Tyr Ala Gln Ala Gly Ala Asp Val Ala Ile Trp Tyr Asn Ser Thr Asn
    50                  55                  60

Ala Asp His Glu Ala Glu Arg Leu Ser Lys Thr Tyr Gly Ile Arg Ala
65                  70                  75                  80

Lys Ala Tyr Lys Cys Ala Val Gly Asp Phe Asp Gln Val Lys Ala Thr
                85                  90                  95

Ile Asp Ala Ile Glu Ser Asp Phe Gly Thr Ile His Ile Phe Val Ala
            100                 105                 110

Asn Ala Gly Ile Gly Ser Gln Ser Val Pro Val Ile Asp Ala Ser Leu
        115                 120                 125

Glu Lys Tyr Arg Ala Ile Met Asn Thr Asn Leu Asp Gly Val Tyr Tyr
    130                 135                 140

Cys Ala Lys Cys Val Gly Pro Ile Phe Lys His Gly Lys Gly Ser
145                 150                 155                 160

Phe Ile Ile Thr Thr Ser Gln Ala Ala His Ile Val Thr Ala His Val
                165                 170                 175

Trp Gln Ala Ala Tyr Asn Ala Ser Lys Ala Ala Cys Ile Gln Ile Ala
            180                 185                 190

Lys Ser Leu Ala Met Glu Trp Val Gly Phe Ala Arg Val Asn Thr Ile
        195                 200                 205

Ser Pro Gly Tyr Ile Val Thr Pro Ile Ser Lys Asp Val Pro Asn Glu
    210                 215                 220

Glu Lys Val Lys Trp Cys Thr Leu Ile Pro Met Gly Arg Glu Gly Leu
225                 230                 235                 240

Pro Gln Glu Leu Val Gly Ala Tyr Leu Tyr Phe Ala Ser Asp Ala Ser
                245                 250                 255
```

```
Thr Phe Thr Thr Gly Ala Asp Leu Ile Ile Asp Gly Gly Tyr Cys Cys
        260                 265                 270
Pro
```

<210> SEQ ID NO 3
<211> LENGTH: 1425
<212> TYPE: DNA
<213> ORGANISM: Flavobacterium fuscum

<400> SEQUENCE: 3

```
atggctgaac aattcgacgt cgtcgtcatc ggtgccggcc cggccggcta ccatgccgcc    60
atccgcgctg cccagctggg cttgaagacc gcctgcatcg atgccgcgct gggcaaggac   120
ggcaagccgg ccctgggcgg cacctgcctg cgcgtgggct gcatcccgtc caaggcgctg   180
ctggattcct cgcgccagtt ctggaacatg gccacatct tcggcgagca cggcatcagc   240
ttcgacaatg ccggcatcga cgtggaaaag atggttggcc gcaaggacgc catcgtcaag   300
cagttcaccg gcggcatcgc gatgctgttc aaggccaaca aggttgccac ctactacggc   360
ttcggccagc tgcaggccgg caatgtggtc accgtgaccc agcacgatgg ttcggtggtt   420
gagctcaagg gcaccaacgt catcatcgcc gccggctcgg actcgatcga gctgccgttt   480
gccaagttcg acggcaagca catcgtcgac aacgtcggcg cgctggattt caccgagacc   540
ccgaagcgcc tgggcgtgat cggtgccggc gtgatcggtc tggagctggg ctcggtctgg   600
aagcgtctgg gttcggaagt caccatcctg gaagccgcgc cgaacttcct ggccgctgcc   660
gacgccgaag tggccaagct ggccgcgcgt gaattcaaga agcagggcct ggacatcaag   720
ctcggcgcca agctggccaa ggccgaagtg gtcggcgacg aagtcgtgct gacctacaac   780
gacgccaatg cgagcagac cctgaccgtg acaagctgc tggtggccgt cggccgcaag   840
gccgcctcca agggcctgct gggcgaaggc tgccaggtca agctcaacga gcgtggccag   900
atcatcgttg acgagcactg ccacaccggc gtggacggc tctgggccgt gggtgactgc   960
gtgcgcgggc cgatgctggc gcacaagggc ttcgaggaag gcatcgcggt ggccgaactg  1020
atcgccggcc tgccgggtca cgtcaacttc gacaccatcc cgtgggtgat ctacaccgag  1080
ccggagctgg cctgggtcgg caagaccgaa cagcagctca aggacgaggg catcccgtac  1140
aaggccggca gcttcccgtt cgccgccaac ggccgtgccg tggcgatggt cgagccggcc  1200
ggtttcgtca aggtcctggc ccacgccgag accgaccgcg tgctcggcat gcacctggtt  1260
ggcgccaatg tctccgagct ggtgcacgaa ggtgtgctga ccatggagtt cagcggctcg  1320
gccgatgacc tggcacgcat ctgccacgcc cacccgtcgc tgtcggaagt gattcacgac  1380
gcggcgatgg cggtgagcaa gcgcgccatc cacaagacca actga             1425
```

<210> SEQ ID NO 4
<211> LENGTH: 474
<212> TYPE: PRT
<213> ORGANISM: Flavobacterium fuscum

<400> SEQUENCE: 4

```
Met Ala Glu Gln Phe Asp Val Val Val Ile Gly Ala Gly Pro Ala Gly
1               5                   10                  15

Tyr His Ala Ala Ile Arg Ala Ala Gln Leu Gly Leu Lys Thr Ala Cys
            20                  25                  30

Ile Asp Ala Ala Leu Gly Lys Asp Gly Lys Pro Ala Leu Gly Gly Thr
        35                  40                  45
```

```
Cys Leu Arg Val Gly Cys Ile Pro Ser Lys Ala Leu Leu Asp Ser Ser
 50                  55                  60

Arg Gln Phe Trp Asn Met Gly His Ile Phe Gly Glu His Gly Ile Ser
 65                  70                  75                  80

Phe Asp Asn Ala Gly Ile Asp Val Glu Lys Met Val Gly Arg Lys Asp
                 85                  90                  95

Ala Ile Val Lys Gln Phe Thr Gly Gly Ile Ala Met Leu Phe Lys Ala
            100                 105                 110

Asn Lys Val Ala Thr Tyr Tyr Gly Phe Gly Gln Leu Gln Ala Gly Asn
            115                 120                 125

Val Val Thr Val Thr Gln His Asp Gly Ser Val Val Glu Leu Lys Gly
130                 135                 140

Thr Asn Val Ile Ile Ala Ala Gly Ser Asp Ser Ile Glu Leu Pro Phe
145                 150                 155                 160

Ala Lys Phe Asp Gly Lys His Ile Val Asp Asn Val Gly Ala Leu Asp
                165                 170                 175

Phe Thr Glu Thr Pro Lys Arg Leu Gly Val Ile Gly Ala Gly Val Ile
            180                 185                 190

Gly Leu Glu Leu Gly Ser Val Trp Lys Arg Leu Gly Ser Glu Val Thr
            195                 200                 205

Ile Leu Glu Ala Ala Pro Asn Phe Leu Ala Ala Asp Ala Glu Val
210                 215                 220

Ala Lys Leu Ala Ala Arg Glu Phe Lys Lys Gln Gly Leu Asp Ile Lys
225                 230                 235                 240

Leu Gly Ala Lys Leu Ala Lys Ala Glu Val Val Gly Asp Glu Val Val
            245                 250                 255

Leu Thr Tyr Asn Asp Ala Asn Gly Glu Gln Thr Leu Thr Val Asp Lys
            260                 265                 270

Leu Leu Val Ala Val Gly Arg Lys Ala Ala Ser Lys Gly Leu Leu Gly
            275                 280                 285

Glu Gly Cys Gln Val Lys Leu Asn Glu Arg Gly Gln Ile Ile Val Asp
            290                 295                 300

Glu His Cys His Thr Gly Val Asp Gly Val Trp Ala Val Gly Asp Cys
305                 310                 315                 320

Val Arg Gly Pro Met Leu Ala His Lys Gly Phe Glu Glu Gly Ile Ala
                325                 330                 335

Val Ala Glu Leu Ile Ala Gly Leu Pro Gly His Val Asn Phe Asp Thr
            340                 345                 350

Ile Pro Trp Val Ile Tyr Thr Glu Pro Glu Leu Ala Trp Val Gly Lys
            355                 360                 365

Thr Glu Gln Gln Leu Lys Asp Glu Gly Ile Pro Tyr Lys Ala Gly Ser
            370                 375                 380

Phe Pro Phe Ala Ala Asn Gly Arg Ala Val Ala Met Val Glu Pro Ala
385                 390                 395                 400

Gly Phe Val Lys Val Leu Ala His Ala Glu Thr Asp Arg Val Leu Gly
                405                 410                 415

Met His Leu Val Gly Ala Asn Val Ser Glu Leu Val His Glu Gly Val
            420                 425                 430

Leu Thr Met Glu Phe Ser Gly Ser Ala Asp Asp Leu Ala Arg Ile Cys
            435                 440                 445
```

His Ala His Pro Ser Leu Ser Glu Val Ile His Asp Ala Ala Met Ala
    450                 455                 460

Val Ser Lys Arg Ala Ile His Lys Thr Asn
465                 470

<210> SEQ ID NO 5
<211> LENGTH: 558
<212> TYPE: DNA
<213> ORGANISM: Pseudomonas putida

<400> SEQUENCE: 5

```
atggctaatt caagaactgc cctcatcatc ggcgcctcgc gcgggcttgg cctgggcttg      60
gtacaacgcc tgcacgaaga cggctggcac atcactgcca ccgtccgtaa cccgcagcag     120
cccggcgacc tggcgaacgt gcccggcgtg cgcatcgagc agttggaaat gaacgacacc     180
gtccagctcg atgacctgaa gcaacgcctg caaggccagg tgttcgacct gatattcgtc     240
aacgccgggg ttatgggccc cctgccgcaa gacctggagg cggtacgcaa caacgacatt     300
ggcgatctgt tcatgactaa cgccgtggcg ccgatacgcg tggctcgccg cctggtgggt     360
caaatacgcg aaggcagcgg tgtgctggcc ttcatgagct cgatcctggg aagcgtcacc     420
ataccngacg ggggcgagat ctgcctgtac aaggccagca aggcggcact gaactcgatg     480
atcaacagct tcttcgttga gcagcagcgc ccggacctgt gcgtgctggc catgcacccg     540
gggctgggtg aaaactga                                                   558
```

<210> SEQ ID NO 6
<211> LENGTH: 185
<212> TYPE: PRT
<213> ORGANISM: Pseudomonas putida

<400> SEQUENCE: 6

Met Ala Asn Ser Arg Thr Ala Leu Ile Ile Gly Ala Ser Arg Gly Leu
1               5                   10                  15

Gly Leu Gly Leu Val Gln Arg Leu His Glu Asp Gly Trp His Ile Thr
            20                  25                  30

Ala Thr Val Arg Asn Pro Gln Gln Pro Gly Asp Leu Ala Asn Val Pro
        35                  40                  45

Gly Val Arg Ile Glu Gln Leu Glu Met Asn Asp Thr Val Gln Leu Asp
    50                  55                  60

Asp Leu Lys Gln Arg Leu Gln Gly Gln Val Phe Asp Leu Ile Phe Val
65                  70                  75                  80

Asn Ala Gly Val Met Gly Pro Leu Pro Gln Asp Leu Glu Ala Val Arg
                85                  90                  95

Asn Asn Asp Ile Gly Asp Leu Phe Met Thr Asn Ala Val Ala Pro Ile
            100                 105                 110

Arg Val Ala Arg Arg Leu Val Gly Gln Ile Arg Glu Gly Ser Gly Val
        115                 120                 125

Leu Ala Phe Met Ser Ser Ile Leu Gly Ser Val Thr Ile Pro Asp Gly
    130                 135                 140

Gly Glu Ile Cys Leu Tyr Lys Ala Ser Lys Ala Ala Leu Asn Ser Met
145                 150                 155                 160

Ile Asn Ser Phe Phe Val Glu Gln Gln Arg Pro Asp Leu Cys Val Leu
                165                 170                 175

Ala Met His Pro Gly Leu Gly Glu Asn
            180                 185

-continued

```
<210> SEQ ID NO 7
<211> LENGTH: 939
<212> TYPE: DNA
<213> ORGANISM: Hansenula polymorpha

<400> SEQUENCE: 7
atggcttcta tttgcacaaa gactcaaaag ctcaacactg gcgcctcaat cccttcagtt    60
gccctgggat gctggcaatc gtcccccgag gacacctaca cttctgtttt ggccgcattg   120
aaggcaggct acagacatat cgacaccgcg cacgtgtacc ggaacgaggc ggatgttggt   180
agagccatca aagactcggg ggttcctaga gagtcgctct tcatcactac gaagctctgg   240
aacaccaacc acagagaccc attggctgct ctgaatggct cgttggagag actcggcatg   300
gattacgtcg atctgtatct ggtgcactgg cctgttcctt ttgttaagcc ttcgccagat   360
gccgaggaac agtggttccc aaaggatcct aacaatccgg aaaagttcca caatgacaaa   420
gattgggact tcatcaagac gtgggaactg gtccaacagc tgcctaagga caaggcccgg   480
gccgtgggcg tgtctaacat gtccaagaca aacttggaga agctgctagc tgcgccaacg   540
accaaggtcg ttcctgcagc caaccaggtc gaaatgcacc cattctaccc cgcgccaccag   600 ctgctcgagt actgcaagga gaaaggcatt gttgtggagg cgtactcgcc actgggcagt   660
gctgggtcgc cactacttaa ggacgaggac atcattgctc tcgccgacaa gaagggcatt   720
tctccagcct gtctgctgat ttcgtgggct cttcacagag acactgtcgt gctgccaaag   780
agcgtgactc cgtcgcggat cgaggccaac atcaaggtcg tcgacctcga cgacgagacc   840
gctgacgccc tgtcggcgct ctacaagacc aagggtagaa gaattctgaa ccctgactgg   900
ggtgttccag tctacaacga cgaagaagac aactttttag                          939

<210> SEQ ID NO 8
<211> LENGTH: 312
<212> TYPE: PRT
<213> ORGANISM: Hansenula polymorpha

<400> SEQUENCE: 8

Met Ala Ser Ile Cys Thr Lys Thr Gln Lys Leu Asn Thr Gly Ala Ser
  1               5                  10                  15

Ile Pro Ser Val Ala Leu Gly Cys Trp Gln Ser Ser Pro Glu Asp Thr
             20                  25                  30

Tyr Thr Ser Val Leu Ala Ala Leu Lys Ala Gly Tyr Arg His Ile Asp
         35                  40                  45

Thr Ala His Val Tyr Arg Asn Glu Ala Asp Val Gly Arg Ala Ile Lys
     50                  55                  60

Asp Ser Gly Val Pro Arg Glu Ser Leu Phe Ile Thr Thr Lys Leu Trp
 65                  70                  75                  80

Asn Thr Asn His Arg Asp Pro Leu Ala Ala Leu Asn Gly Ser Leu Glu
                 85                  90                  95

Arg Leu Gly Met Asp Tyr Val Asp Leu Tyr Leu Val His Trp Pro Val
            100                 105                 110

Pro Phe Val Lys Pro Ser Pro Asp Ala Glu Glu Gln Trp Phe Pro Lys
        115                 120                 125

Asp Pro Asn Asn Pro Glu Lys Phe His Asn Asp Lys Asp Trp Asp Phe
    130                 135                 140

Ile Lys Thr Trp Glu Leu Val Gln Gln Leu Pro Lys Asp Lys Ala Arg
145                 150                 155                 160

Ala Val Gly Val Ser Asn Met Ser Lys Thr Asn Leu Glu Lys Leu Leu
                165                 170                 175
```

-continued

```
Ala Ala Pro Thr Thr Lys Val Val Pro Ala Ala Asn Gln Val Glu Met
            180             185                 190

His Pro Phe Tyr Pro Arg His Gln Leu Leu Glu Tyr Cys Lys Glu Lys
        195             200                 205

Gly Ile Val Val Glu Ala Tyr Ser Pro Leu Gly Ser Ala Gly Ser Pro
        210             215                 220

Leu Leu Lys Asp Glu Asp Ile Ile Ala Leu Ala Asp Lys Lys Gly Ile
225             230                 235                 240

Ser Pro Ala Cys Leu Leu Ile Ser Trp Ala Leu His Arg Asp Thr Val
            245                 250                 255

Val Leu Pro Lys Ser Val Thr Pro Ser Arg Ile Glu Ala Asn Ile Lys
            260             265                 270

Val Val Asp Leu Asp Asp Glu Thr Ala Asp Ala Leu Ser Ala Leu Tyr
            275             280                 285

Lys Thr Lys Gly Arg Arg Ile Leu Asn Pro Asp Trp Gly Val Pro Val
            290             295                 300

Tyr Asn Asp Glu Glu Asp Asn Phe
305                 310
```